(12) United States Patent  (10) Patent No.: US 8,411,816 B2
Ohara  (45) Date of Patent: Apr. 2, 2013

(54) RADIOLOGICAL IMAGE CAPTURING APPARATUS AND RADIOLOGICAL IMAGE CAPTURING SYSTEM

(75) Inventor: Hiromu Ohara, Tokyo (JP)

(73) Assignee: Konica Minolta Medical & Graphic, Inc. (JP)

( * ) Notice: Subject to any disclaimer, the term of this patent is extended or adjusted under 35 U.S.C. 154(b) by 152 days.

(21) Appl. No.: 12/527,673

(22) PCT Filed: Feb. 14, 2008

(86) PCT No.: PCT/JP2008/052422
§ 371 (c)(1),
(2), (4) Date: Aug. 18, 2009

(87) PCT Pub. No.: WO2008/102685
PCT Pub. Date: Aug. 28, 2008

(65) Prior Publication Data
US 2010/0119041 A1  May 13, 2010

(30) Foreign Application Priority Data

Feb. 21, 2007 (JP) ................................. 2007-041437
Feb. 21, 2007 (JP) ................................. 2007-041440
Feb. 21, 2007 (JP) ................................. 2007-041446

(51) Int. Cl.
*G03H 5/00* (2006.01)
*G01N 23/205* (2006.01)
(52) U.S. Cl. .......................................... 378/36; 378/62
(58) Field of Classification Search ................ 378/2, 36, 378/62, 145
See application file for complete search history.

(56) References Cited

U.S. PATENT DOCUMENTS 5,812,629 A * 9/1998 Clauser ........................... 378/62
7,180,979 B2 * 2/2007 Momose ......................... 378/62
7,532,704 B2 * 5/2009 Hempel .......................... 378/19
7,693,256 B2 * 4/2010 Brahme et al. ................. 378/41
(Continued)

FOREIGN PATENT DOCUMENTS

JP         3-167413 A     7/1991
JP    2004-248699 A     9/2004
(Continued)

OTHER PUBLICATIONS

International Search Report for Application No. PCT/JP2008/052422 mailed May 13, 2008 with English translation.

*Primary Examiner* — Thomas R Artman
(74) *Attorney, Agent, or Firm* — Cantor Colburn LLP

(57) ABSTRACT

There is described a radiological image capturing apparatus, which makes it possible to obtain a good X ray image in which contrast of the peripheral portions are emphasized by employing the Talbot interferometer method and the Talbot-Lau interferometer method. The apparatus is provided with an X-ray tube, a multi-slit member, a first diffraction grating, a second diffraction grating and an X-ray detector. The second diffraction grating contacts the X-ray detector. A distance L between the multi-slit element and the first diffraction grating is set to be not less than 0.5 m, a distance $Z_1$ between the first diffraction grating and the second diffraction grating is set to be not less than 0.05 m, and a slit interval distance $d_0$ of the multi-slit element is set to be not less than 2 μm. With the settings, the abovementioned good X-ray image can be obtained by using the Talbot-Lau interferometer system.

2 Claims, 8 Drawing Sheets

U.S. PATENT DOCUMENTS

| | | | |
|---|---|---|---|
| 7,889,838 B2 * | 2/2011 | David et al. | 378/36 |
| 2005/0053192 A1 * | 3/2005 | Sukovic et al. | 378/41 |
| 2006/0039532 A1 * | 2/2006 | Wu et al. | 378/62 |
| 2009/0092227 A1 * | 4/2009 | David et al. | 378/36 |
| 2010/0080436 A1 * | 4/2010 | Ohara | 382/132 |

FOREIGN PATENT DOCUMENTS

WO 2004058070 A1 7/2004

* cited by examiner

RADIOLOGICAL IMAGE CAPTURING APPARATUS AND RADIOLOGICAL IMAGE CAPTURING SYSTEM

CROSS REFERENCE TO RELATED APPLICATIONS

This is a U.S. national stage of application No. PCT/JP2008/052422, filed on 14 Feb. 2008. Priority under 35 U.S.C. §119(a) and 35 U.S.C. §365(b) is claimed from Japanese Application No. 2007-041437, filed 21 Feb. 2007, Japanese Application No. 2007-041440, filed 21 Feb. 2007, and Japanese Application No. 2007-041446, filed 21 Feb. 2007, the disclosure of which is also incorporated herein by reference.

FIELD OF THE INVENTION

The present invention relates to a radiological image capturing apparatus and a radiological image capturing system, and specifically relates to such a radiological image capturing apparatus that employs a Talbot-Lau interferometer method and such a radiological image capturing system that applies various kinds of processing to an image captured by the radiological image capturing apparatus.

TECHNICAL BACKGROUND

In recent years, the morbidity rate of the rheumatic disease in Japan has reached to 1% of the national population, and accordingly, the rheumatic disease has been regarded as a kind of a folk disease at present. An abrasion loss at a cartilage portion (destruction of cartilage) and/or subtle changes of a bone shape and a bone trabeculae are observed as its early symptoms, and then, at the time when the symptoms have worsened, considerable changes of shape of the bone sections can be observed significantly.

Accordingly, by observing the shape of cartilage portion and subtle changes of the bone shape and the bone trabeculae, it is possible to make a diagnosis with respect to the disease situation of the rheumatic disease at its early stage. Considering the actual condition that only medical treatments for stopping the progress of the symptoms are currently available as the medical treatments for the rheumatic disease, it is important to detect the rheumatic disease at its early stage and to speedily shift the patient into the phase of applying the medical treatments.

However, the above-mentioned early symptoms of the rheumatic disease have been hardly detected by observing the X-ray photographic image, which has been widely accepted as a simple and convenient inspection method, and accordingly, it has been difficult for a doctor or the like to determine whether or not the rheumatic disease has actually developed.

On the other hand, in recent years, instead of the radiographic images acquired by radiographing the patient, images acquired by employing the MRI (Magnetic Resonance Imaging) has been considered as a tool for making diagnosis, in order to detect the changes of cartilage tissues. Further, recently, in the field of the radiographic image capturing technologies, there has been reported such a technology that extracts a radiant beam, which straightly progress in parallel, so that the above-extracted radiant beam are used for capturing images of the cartilage portion concerned. However, since the patient has been heavily burdened with the MRI photographing operation from the viewpoint of the cost and time required for making a diagnosis, it has been difficult to perform the MRI photographing operation in the framework of the regular physical examination. Therefore, there has been such a problem that it has been difficult to periodically perform the MRI photographing operation so as to observe (inspect) the changes of the joint portions, such as fingers, etc., over time, as a longitudinal diagnosis.

Further, since a huge image-capturing installation is necessary for conducting the image-capturing operation that employs the radiant beam, and, sometimes, several tens of minutes are required for completing the image-capturing operation, it has been virtually impossible for a general-purpose medical facility to employ the radiant beam for conducting the image-capturing operation. Due to the present situations as aforementioned, it has been desired to make it possible to simply and easily make a diagnosis on the diseases of cartilage portion at its early stage, such as a subtle change in a shape of joint portion, a subtle change in the bone shape, a swelling, etc.

For instance, in order to make a diagnosis on the case of the rheumatic diseases at its early stage, it is indispensable to capture such a radiographic image that has a high sharpness being sufficient for recognizing a subtle change of a symptom in the patient, represented thereon. As the radiological image capturing apparatus that can capture a radiographic image having a sufficiently high sharpness, there has been well-known the technology for capturing a phase contrast image by employing the radiological image capturing apparatus, for instance, set forth in Patent Document 1. According to the technology set forth in Patent Document 1, even for such a subject whose X-ray absorbing rate is specifically lower than other subjects to such an extent that its radiological image having a sufficient contrast cannot be formed by employing the normal X-ray absorbing action, it has been possible to obtain such an radiological image in which contrast of the peripheral portions (edge portions) are specifically emphasized. Further, it has bee possible to apply the above-mentioned technology not only to joint disorders, which are represented by the rheumatic disease, but also to various kinds of sections, such as a breast image capturing operation that should be capable of detecting a micro calcification from a breast, most of which is formed by a soft tissue, an operation for radiographing a child body, almost bones of which are cartilages, etc.

Further, as the technology for further emphasizing the contrast of the peripheral portions of the subject, for instance, Patent Document 2 sets forth an X ray radiographing apparatus employing the Talbot interferometer method based on the Talbot effect caused by the diffraction grating. Still further, Non-patent Document 1 sets forth an X ray radiographing method employing the Talbot-Lau interferometer method, which is improved from the Talbot interferometer method.

[Patent Document 1] Tokkai 2004-248699 (Japanese Laid-open Non-Examined Patent Publication)
[Patent Document 2] WO 2004-058070 (International Publication)
[Non-patent Document 1] "RECENT DEVELOPMENT OF X RAY PHASE IMAGING" written by Atsushi Momose, Medical Imaging Technology, Japanese Society of Medical Imaging Technology, November, 2006, vol. 24, No. 5, page 359-366

However, since the radiant beam X ray source, which requires a special facility, is employed in the Talbot interferometer method set forth in Patent Document 2, there has been a problem that it is virtually impossible for general-purpose medical facilities, widely exiting in the society, to employ the Talbot interferometer method. In addition, in such the general-purpose medical facilities, it has been assumed that low energy X rays are to be irradiated onto the subject. This is because, the phase contrast effect, acquired by employing the low energy X rays, is relatively great, and the absorbing contrast effect, acquired by employing the conventional X rays radiological imaging, is relatively strong. However, since the excessively low energy X-rays tend to be absorbed into the human body, and accordingly, since an amount of the X rays arriving at a detector is relatively small, it is necessary to increase the dose of radiation exposure in order to acquire an appropriate S/N (Signal to Noise) ratio at the detector, resulting in an increase of the X-ray exposure. Further, the increase of the X-ray exposure will cause an extension of the image capturing time interval. However, it is difficult to make the movement of the human body, serving as the subject, freeze for a long time during the image capturing time interval. Then, as a result of the movements of the subject during the radiographing, an X-ray image in which the peripheral sections of the subject are blurred would be captured, and accordingly, an advantageous characteristic of the Talbot-Lau interferometer that can emphasize the contrast of peripheral sections of the subject would be deteriorated.

On the other hand, if the energy of the X rays to be irradiated onto the human body is excessively high, it has been acquired such a knowledge that an image contrast being sufficient for depicting bone tissues and soft tissues that constitute the human body cannot be obtained. Accordingly, there has been a problem that an X ray image, which is sufficiently usable for making a diagnosis on the human body, serving as the subject, cannot be obtained, unless the contrast in the X ray image can be obtained.

As abovementioned, when the radiological image capturing apparatus in conformity with the Talbot interferometer method is employed for the medical purpose, a usable range of the X ray radiation energy (precisely speaking, average energy) is relatively narrow. In addition, in order to generate the Talbot effect so as to realize the Talbot interferometer method, various kinds of strict limitations are applied to a distance between a first diffraction grating and a second diffraction grating, an interval (grating period) between diffraction elements constituting the each of the diffraction gratings, etc., as detailed later. Therefore, in order to apply the Talbot interferometer method to an operation for radiographing the various kinds of sections in the human body, specifically for such the sections that are hardly captured by the X-ray image capturing method, such as the cartilage tissue, etc., the radiological image capturing apparatus should be configured so as to fulfill the extremely strict conditions.

Further, according to the Talbot-Lau interferometer method set forth in Non-patent Document 1, a multi-slit element is disposed between the X ray source to be employed in the Talbot interferometer method and the subject. Since the X ray emitting source is converted to multi (plural) radiant sources by employing the multi-slit element, it is possible to effectively utilize the Talbot effect, even if the X ray tube having a large focal diameter is employed in the apparatus. However, the structure and configuration of the concerned apparatus become more complicated than ever, and, further, since various kinds of conditions, such as positional relationships between the multi-slit element and the other elements, etc., are added as new limitations for configuring the apparatus, the structural conditions for the concerned apparatus become still more stricter than ever, and it is required for the concerned apparatus to fulfill such the extremely strict conditions.

On the other hand, a dose of X rays, to be irradiated onto the subject by the radiological image capturing apparatus employing the Talbot interferometer method, is relatively small, compared to that to be irradiated by the other radiological image capturing apparatus employing the Talbot-Lau interferometer method. However, since the X rays are irradiated by a single X-ray emitting source, the radiological image capturing apparatus employing the Talbot interferometer method has such the advantage that a very clear X-ray image, sharpness of which is very high, can be obtained. Whereas, since the X ray emitting source is converted to the multi (plural) radiant sources by employing the multi-slit element, the Talbot-Lau interferometer method is inferior to the Talbot interferometer method in sharpness of the reproduced X ray image to some extent. However, since it is possible in the Talbot-Lau interferometer method to irradiate relatively high energy X rays onto the subject, compared to the Talbot interferometer method, the radiological image capturing apparatus employing the Talbot-Lau interferometer method has such the advantage that the X-ray radiographing operation can be completed within a shorter time than ever.

Further, if a single radiological image capturing apparatus is so constituted that the abovementioned two methods are provided within the single apparatus so as to make it possible to selectively change them to each other, for instance, by selecting one of the methods corresponding to the current purpose of capturing the X-ray image, it becomes possible to obtain the X-ray image to which the advantage of the selected method is fully applied, resulting in a very convenient apparatus. Still further, if the apparatus concerned is constituted as abovementioned, it becomes possible to appropriately make a diagnosis by adaptively selecting either the Talbot interferometer method or the Talbot-Lau interferometer method.

As aforementioned, it has been desired that the Talbot interferometer method or the Talbot-Lau interferometer method is employed for operations not only for capturing X-ray images of the joint disorders, which are represented by the rheumatic disease, but also for capturing X-ray images of various kinds of sections in human body, such as the breast image capturing operation that should be capable of detecting the micro calcification from the breast, most of which is formed by the soft tissue, an operation for radiographing the child body, almost bones of which are cartilages, etc. However, in order to achieve the abovementioned goals, it is indispensable to configure the apparatus so as to fulfill such the extremely strict conditions as aforementioned.

SUMMARY OF THE INVENTION

To overcome the abovementioned drawbacks in conventional radiological image capturing apparatuses and systems, it is one of objects of the present invention to provide a radiological image capturing apparatus, which makes it possible to obtain a good X ray image in which contrast of the peripheral portions (edge portions), such as a cartilage tissue of human body, etc., are emphasized by employing the Talbot interferometer method and the Talbot-Lau interferometer method, and to provide a radiological image capturing system in which the above-captured X ray image is processed.

Accordingly, at least one of the objects of the present invention can be attained by any one of the radiological image capturing apparatuses and the radiological image capturing systems described as follows.

(1) According to a radiological image capturing apparatus reflecting an aspect of the present invention, the radiological image capturing apparatus, comprises: an X ray tube to emit X rays having an average energy in a range of 15-60 keV; a subject placing plate to place a subject thereon; a multi-slit element that is disposed at a position located on an optical path of the X rays, emitted by the X ray tube, and that has plural slits formed therein; a first diffraction grating to diffract the X rays penetrated through the subject, so as to yield a Talbot effect; a second diffraction grating to diffract the X rays diffracted by the first diffraction grating; and an X-ray detector to detect the X rays diffracted by the second diffraction grating; wherein the multi-slit element and the second diffraction grating are in contact with each other; and wherein a first distance between the multi-slit element and the first diffraction grating, a second distance between the first diffraction grating and the second diffraction grating, and a slit interval distance of the multi-slit element are set at a value equal to or greater than 0.5 m, a value equal to or greater than 0.05 m and a value equal to or greater than 2 µm, respectively.

(2) According to another aspect of the present invention, the radiological image capturing apparatus, recited in item 1, further comprises: a control device that compares a Moiré stripe image, captured before an actual operation of the radiological image capturing apparatus is commenced, with another Moiré stripe image captured after the actual operation of the radiological image capturing apparatus is commenced, to determine whether or not a distortion is generated in a diffraction member of the first diffraction grating or the second diffraction grating.

(3) According to still another aspect of the present invention, in the radiological image capturing apparatus recited in item 1, the control device issues a warning notification corresponding to a result of determining whether or not the distortion is generated.

(4) According to still another aspect of the present invention, the radiological image capturing apparatus, recited in item 1, further comprises: a first temperature sensor to measure a first temperature of the first diffraction grating; a second temperature sensor to measure a second temperature of the second diffraction grating; and a control device to determine whether or not at least one of the first temperature and the second temperature, measured through the first temperature sensor and/or the second temperature sensor, is equal to or greater than a reference temperature established in advance.

(5) According to still another aspect of the present invention, in the radiological image capturing apparatus recited in item 4, the control device issues a warning notification corresponding to a result of determining whether or not at least one of the first temperature and the second temperature is equal to or greater than the reference temperature.

(6) According to still another aspect of the present invention, in the radiological image capturing apparatus recited in item 1, the first diffraction grating, the second diffraction grating and the X-ray detector are made to rotate around a peripheral space of the subject, so as to continuously capture X ray images of the subject from various directions.

(7) According to still another aspect of the present invention, in the radiological image capturing apparatus recited in item 1, the multi-slit element is capable of entering into and withdrawing from the optical path of the X rays emitted by the X ray tube; and the radiological image capturing apparatus further comprising: a control device to control the multi-slit element to enter into and withdraw from the optical path.

(8) According to still another aspect of the present invention, in the radiological image capturing apparatus recited in item 7, when the multi-slit element is disposed at the position located on the optical path, the control device sets the first distance between the multi-slit element and the first diffraction grating at a value equal to or greater than 0.5 m, while, when the multi-slit element withdraws from the optical path, the control device sets a third distance between the X ray tube and the first diffraction grating at a value equal to or greater than 0.5 m and sets a focal point diameter of the X ray tube at a value equal to or greater than 1 µm.

(9) According to still another aspect of the present invention, in the radiological image capturing apparatus recited in item 7, the control device is configured to detect an abnormal shadow candidate from the X ray image captured, so as to change a Talbot-Lau interferometer method to a Talbot interferometer method when detecting the abnormal shadow candidate, as a method to be currently employed in the radiological image capturing apparatus.

(10) According to a radiological image capturing apparatus reflecting still another aspect of the present invention, the radiological image capturing apparatus, comprises: an X ray tube to emit X rays having an average energy in a range of 15-60 keV; a subject placing plate to place a subject thereon; a multi-slit element that is disposed at a position located on an optical path of the X rays, emitted by the X ray tube, and that has plural slits formed therein; a first diffraction grating to diffract the X rays, so as to yield a Talbot effect; a second diffraction grating to diffract the X rays diffracted by the first diffraction grating and penetrated through the subject; and an X-ray detector to detect the X rays diffracted by the second diffraction grating; wherein the multi-slit element and the second diffraction grating are in contact with each other; and wherein a first distance between the multi-slit element and the first diffraction grating, a second distance between the first diffraction grating and the second diffraction grating, and a slit interval distance of the multi-slit element are set at a value equal to or greater than 0.5 m, a value equal to or greater than 0.05 m and a value equal to or greater than 2 µm, respectively.

(11) According to a radiological image capturing system reflecting still another aspect of the present invention, the radiological image capturing system, comprises: a radiological image capturing apparatus that is provided with: an X ray tube to emit X rays having an average energy in a range of 15-60 keV; a subject placing plate to place a subject thereon; a multi-slit element that is disposed at a position located on an optical path of the X rays, emitted by the X ray tube, and that has plural slits formed therein; a first diffraction grating to diffract the X rays penetrated through the subject, so as to yield a Talbot effect; a second diffraction grating to diffract the X rays diffracted by the first diffraction grating; and an X-ray detector to detect the X rays diffracted by the second diffraction grating; wherein the multi-slit element and the second diffraction grating are in contact with each other; and wherein a first distance between the multi-slit element and the first diffraction grating, a second distance between the first diffraction grating and the second diffraction grating, and a slit interval distance of the multi-slit element are set at a value equal to or greater than 0.5 m, a value equal to or greater than 0.05 m and a value equal to or greater than 2 µm, respectively; an image processing apparatus to apply various kinds of image processing to image data representing an image captured by the radiological image capturing apparatus; and an image outputting apparatus to output the image based on the image data processed by the image processing apparatus.

(12) According to a radiological image capturing system reflecting still another aspect of the present invention, the radiological image capturing system, comprises: a radiological image capturing apparatus that is provided with: an X ray tube to emit X rays having an average energy in a range of 15-60 keV; a subject placing plate to place a subject thereon; a multi-slit element that is disposed at a position located on an optical path of the X rays, emitted by the X ray tube, and that has plural slits formed therein; a first diffraction grating to diffract the X rays, so as to yield a Talbot effect; a second diffraction grating to diffract the X rays diffracted by the first diffraction grating and penetrated through the subject; and an X-ray detector to detect the X rays diffracted by the second diffraction grating; wherein the multi-slit element and the second diffraction grating are in contact with each other; and wherein a first distance between the multi-slit element and the first diffraction grating, a second distance between the first diffraction grating and the second diffraction grating, and a slit interval distance of the multi-slit element are set at a value equal to or greater than 0.5 m, a value equal to or greater than 0.05 m and a value equal to or greater than 2 μm, respectively; an image processing apparatus to apply various kinds of image processing to image data representing an image captured by the radiological image capturing apparatus; and an image outputting apparatus to output the image based on the image data processed by the image processing apparatus.

(13) According to a radiological image capturing system reflecting still another aspect of the present invention, the radiological image capturing system, comprises: a radiological image capturing apparatus that is provided with: an X ray tube to emit X rays having an average energy in a range of 15-60 keV; a subject placing plate to place a subject thereon; a multi-slit element that is disposed at a position located on an optical path of the X rays, emitted by the X ray tube, and that has plural slits formed therein; a first diffraction grating to diffract the X rays penetrated through the subject, so as to yield a Talbot effect; a second diffraction grating to diffract the X rays diffracted by the first diffraction grating; and an X-ray detector to detect the X rays diffracted by the second diffraction grating; wherein the multi-slit element and the second diffraction grating are in contact with each other; and wherein a first distance between the multi-slit element and the first diffraction grating, a second distance between the first diffraction grating and the second diffraction grating, and a slit interval distance of the multi-slit element are set at a value equal to or greater than 0.5 m, a value equal to or greater than 0.05 m and a value equal to or greater than 2 μm, respectively; and a diagnosis assistance apparatus to detect an abnormal shadow candidate from an X ray image captured by the radiological image capturing apparatus; wherein the multi-slit element is capable of entering into and withdrawing from the optical path of the X rays emitted by the X ray tube, and the radiological image capturing apparatus is further provided with a control device to control the multi-slit element to enter into and withdraw from the optical path; and wherein the control device is configured to detect an abnormal shadow candidate from the X ray image captured, so as to change a Talbot-Lau interferometer method to a Talbot interferometer method when the diagnosis assistance apparatus detects the abnormal shadow candidate, as a method to be currently employed in the radiological image capturing apparatus.

(14) According to a radiological image capturing system reflecting yet another aspect of the present invention, the radiological image capturing system, comprises: a radiological image capturing apparatus that is provided with: an X ray tube to emit X rays having an average energy in a range of 15-60 keV; a subject placing plate to place a subject thereon; a multi-slit element that is disposed at a position located on an optical path of the X rays, emitted by the X ray tube, and that has plural slits formed therein; a first diffraction grating to diffract the X rays, so as to yield a Talbot effect; a second diffraction grating to diffract the X rays diffracted by the first diffraction grating and penetrated through the subject; and an X-ray detector to detect the X rays diffracted by the second diffraction grating; wherein the multi-slit element and the second diffraction grating are in contact with each other; and wherein a first distance between the multi-slit element and the first diffraction grating, a second distance between the first diffraction grating and the second diffraction grating, and a slit interval distance of the multi-slit element are set at a value equal to or greater than 0.5 m, a value equal to or greater than 0.05 m and a value equal to or greater than 2 μm, respectively; and a diagnosis assistance apparatus to detect an abnormal shadow candidate from an X ray image captured by the radiological image capturing apparatus; wherein the multi-slit element is capable of entering into and withdrawing from the optical path of the X rays emitted by the X ray tube, and the radiological image capturing apparatus is further provided with a control device to control the multi-slit element to enter into and withdraw from the optical path; and wherein the control device is configured to detect an abnormal shadow candidate from the X ray image captured, so as to change a Talbot-Lau interferometer method to a Talbot interferometer method when the diagnosis assistance apparatus detects the abnormal shadow candidate, as a method to be currently employed in the radiological image capturing apparatus.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE PREFERRED EMBODIMENT

Figure 1:
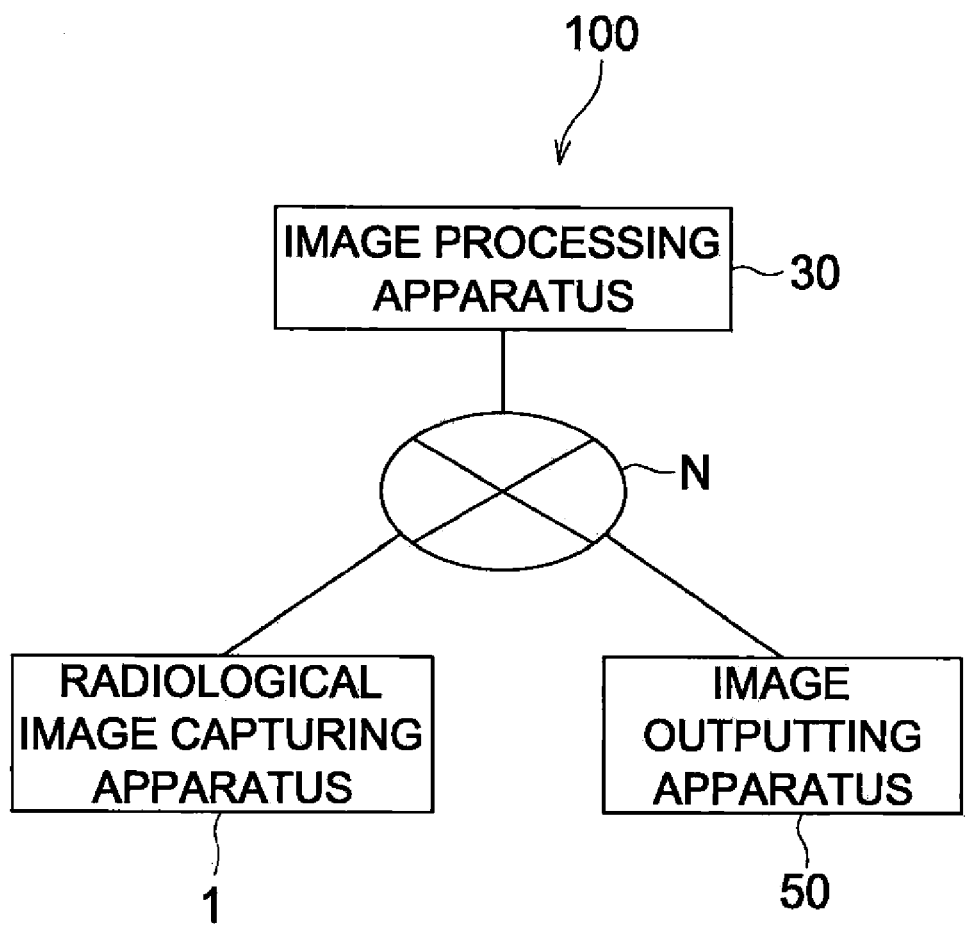
FIG. 1 shows schematic diagram indicating an overall configuration of a radiological image capturing system, embodied in the present invention.

Referring to the drawings, the radiological image capturing apparatus and the radiological image capturing system, both embodied in the present invention, will be detailed in the following. However, the scope of the present invention is not limited to the examples indicated in the drawings.

In the present embodiment, a radiological image capturing system 100 is constituted by: a radiological image capturing apparatus 1 that irradiates X rays, serving as radial rays, onto a subject so as to generate radiological image data of the subject; an image processing apparatus 30 that applies various kinds of image processing to the radiological image data generated by the radiological image capturing apparatus 1; and an image outputting apparatus 50 that outputs a radiological image, etc., onto a display screen or a film, based on processed image data generated by applying the various kinds of image processing to the radiological image data in the image processing apparatus 30. Each of the radiological image capturing apparatus 1, the image processing apparatus 30 and the image outputting apparatus 50 is coupled to a communication network N (hereinafter, referred to as a network N, for simplicity), such as a LAN (Local Area Network), etc., for instance, through a switching hub, etc., (not shown in the drawings).

In this connection, the scope of the configuration of the radiological image capturing system 100 is not limited to the system exemplified in FIG. 1. For instance, it is also applicable that the radiological image capturing system is so constituted that the image processing apparatus 30 and the image outputting apparatus 50 are integrated into a single apparatus, so that the integrated single apparatus conducts both the image processing operations and the radiological image outputting operation (onto the display screen or the film) based on the processed image data.

Figure 2:
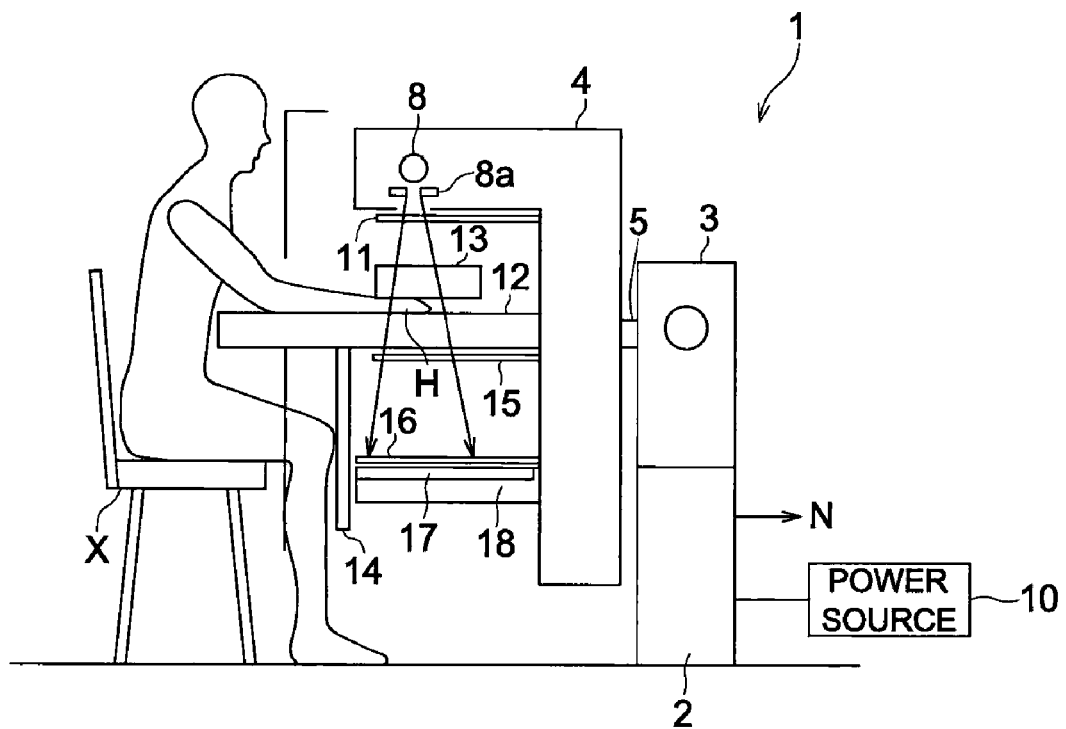
FIG. 2 shows a schematic diagram indicating an exemplary configuration of a radiological image capturing apparatus, embodied in the present invention.
Figure 3:
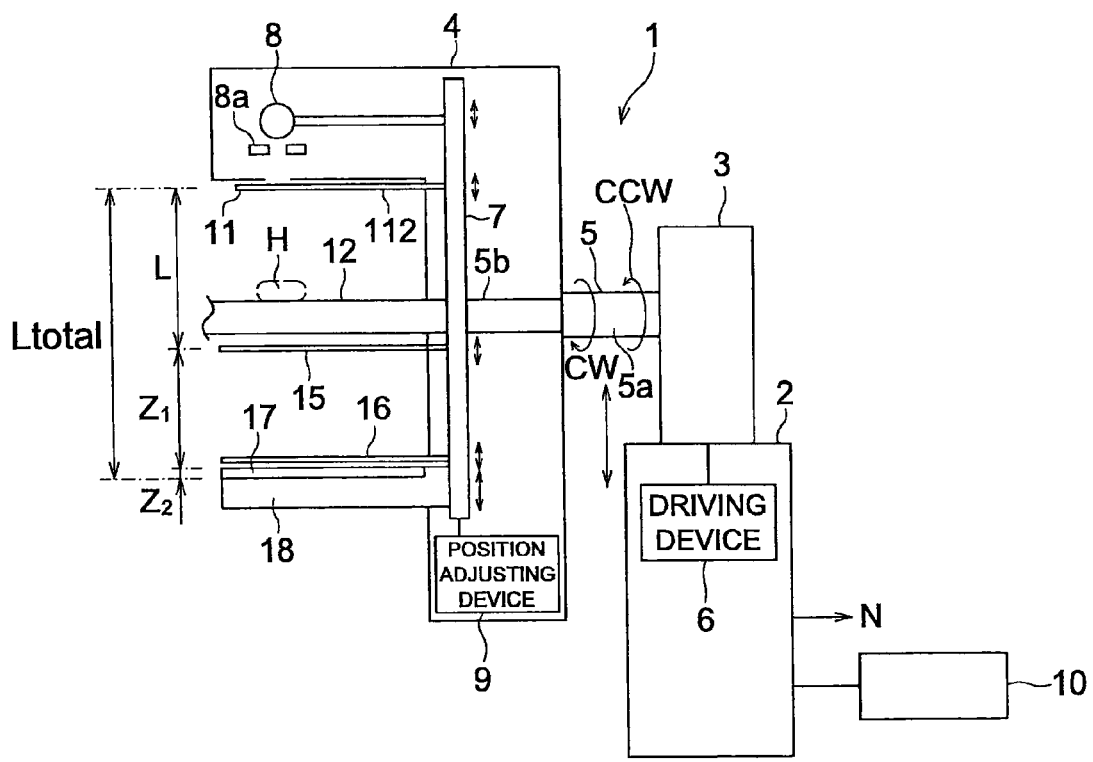
FIG. 3 shows a schematic diagram indicating an internal configuration of a radiological image capturing apparatus, shown in FIG. 2.

As shown in FIG. 2 and FIG. 3, the radiological image capturing apparatus 1 is provided with a base frame 2 that is fixed on the floor surface with bolts or the like and a supporting base member 3 that is movable in both up and down directions relative to the base frame 2. Further, an image capturing main section 4 is supported by the supporting base member 3 through a supporting shaft 5. The supporting shaft 5 is constituted by an outer supporting cylinder 5a shaped in a cylinder and an inner supporting shaft 5b disposed inside the outer supporting cylinder 5a, so as to make the outer supporting cylinder 5a rotatable in either a clockwise direction or a counterclockwise direction around the inner supporting shaft 5b, serving as the rotating axis.

The supporting base member 3 is provided with a driving device 6 for driving its up-and-down movements and the rotational motion of the supporting shaft 5, and the driving device 6 is provided with a conventional driving motor (not shown in the drawings). The image capturing main section 4 is fixed to the outer supporting cylinder 5a so as to elevate or descend synchronized with the up-and-down movements of the supporting base member 3 through the supporting shaft 5. Further, the image capturing main section 4 is rotated around the inner supporting shaft 5b, serving as the rotating axis, by making the outer supporting cylinder 5a rotate in either the clockwise direction or the counterclockwise direction.

A supporting bar member 7, shaped in substantially a bar, is fixed in the image capturing main section 4 in such a manner that the supporting bar member 7 can expand and contract in both up and down directions. An X ray tube 8 that irradiates X rays onto a subject H is disposed at the upper section of the supporting bar member 7 in such a manner that the X ray tube 8 can freely elevate and descend. The X ray tube 8 is driven to elevate or descend by a position adjustment device 9, which is provided with a conventional driving motor, etc. (not shown in the drawings), so as to adjust the position of the X ray tube 8. Further, a power source 10 to supply electric power is coupled to the X ray tube 8 through the supporting base member 3, the supporting shaft 5 and image capturing main section 4. Still further, an aperture 8a to adjust the X-ray irradiation field is disposed at an X-ray irradiation opening of the X ray tube 8 in such a manner that the aperture 8a can be freely opened and closed, and the aperture 8a elevates and descend with the X ray tube 8.

A X ray tube that can irradiate X rays, having an average energy in a range of 15-60 keV, is employed as the X ray tube 8 abovementioned. This is because, when the average energy of the X rays to be irradiated, is smaller than 15 keV, since almost of all part of the irradiated X rays are absorbed into the subject, a dose of X ray exposure becomes extremely great, and accordingly, such the setting is not suitable for clinical use. On the other hand, when the average energy of the X rays to be irradiated, is greater than 60 keV, it has been impossible to acquire such the X-ray radiation image that has sufficient contrasts so as to clearly represent bones, soft tissue sections, etc., which constitute the human body, and therefore, there is a possibility that the acquired X-ray radiation image cannot be used for a medical diagnosis or the like.

It is preferable that, for instance, the Coolidge X-ray tube or the rotation anode X-ray tube, which has been widely used in the actual medical field, is employed as the X ray tube 8. On that occasion, when a molybdenum (Mo) material is employed for the target (anode) of the X-ray tube, as widely employed in the breast image radiographing operation (mammography, in this case, a molybdenum filter, having a thickness of 30 μm, is normally added), generally speaking, the X rays having the average energy of 15 keV are emitted from the X-ray tube at the time when a set voltage of 22 kVp is applied to the X-ray tube concerned, while the X rays having the average energy of 21 keV are emitted from the X-ray tube at the time when a set voltage of 39 kVp is applied to the X-ray tube concerned. Further, when a tungsten (W) material is employed for the target (anode) of the X-ray tube, as widely employed in the normal radiographing operation, generally speaking, the X rays having the average energies of 22, 32, 47 and 60 keV are emitted from the X-ray tube at the time when set voltages of 30, 50, 100 and 150 kVp is applied to the X-ray tube concerned, respectively.

In the case of the radiological image capturing apparatus 1, embodied in the present invention, in which not only operations for radiographing joint disorders, which are represented by the rheumatic disease, but also various kinds of other radiographing operations, such as a breast image radiographing operation that should be capable of detecting a micro calcification from a breast, most of which is formed by a soft tissue, an operation for radiographing a child body, almost bones of which are cartilages, etc., are objects to be conducted, since the sharpness of the captured image can be improved due to the phase contrast effect by irradiating the X rays, specifically having a low X-ray energy (voltage to be applied to the X-ray tube concerned is set at a low voltage), among the X rays having various levels of the average energies, it is preferable that the average energy of the X rays to be irradiated is in a range of 15-32 keV. Further, considering the does of radiation exposure, it is more preferable that the average energy of the X rays to be irradiated is in a range of 20-27 keV. This can be achieved by employing the tungsten (W) material for the target of the X-ray tube concerned.

The radiological image capturing apparatus 1 is so constituted that the Talbot interferometer method and the Talbot-Lau interferometer method, both detailed later, can be selectively changed to each other. When the radiological image capturing apparatus 1 is used as the Talbot interferometer, the focal diameter of the X ray tube 8 is set at such a value that is equal to or greater than 1 µm, so as to irradiate the X rays having the average energy in the abovementioned range and to acquire a practical output intensity. In this connection, in order to acquire a sufficient X-ray intensity, it is preferable that the focal diameter of the X ray tube 8 is set at a value being equal to or greater than 7 µm. Further, the X rays to be incident onto the first diffraction grating, detailed later, should have a coherence property. From the point that the X rays to be employed has the average energy in a range of 15-60 keV, and from the other point that the upper limit of the length of the radiographing apparatus is around 2 meters at the longest as detailed later, it is preferable that the focal diameter of the X ray tube 8 is set at a value being equal to or smaller than 50 µm, in order to posses the coherence property. Further, in order to improve the coherence property and to acquire a clear image by effectively using the Talbot effect detailed later, it is more preferable that the focal diameter of the X ray tube 8 is set at a value being equal to or smaller than 30 µm.

Further, when the radiological image capturing apparatus 1 is used as the Talbot-Lau interferometer, the X rays to be incident onto the first diffraction grating, detailed later, should have a coherence property, as well as the above, and it is preferable that the focal diameter of the X ray tube 8 is set at a smaller value, in order to posses the coherence property. However, according to the present invention, since the X rays emitted by the X ray tube 8 are converted to multi (plural) radiant sources by employing a multi-slit element 11 detailed later, and in addition, the high power outputting capability is required for the X ray tube 8, it is not necessary to make the focal diameter of the X ray tube 8 so small.

Accordingly, in the Talbot-Lau interferometer method embodied in the present invention, the focal diameter of the X ray tube 8 is set at a value being equal to or greater than 10 µm. Concretely speaking, it is preferable that the focal diameter of the X ray tube 8 is in a range of 10-500 µm, and more preferable that the focal diameter of the X ray tube 8 is set at a value being equal to or greater than 50 µm. Practically, the focal diameter is preferably set at a value being in a range of 100-300 µm. In this connection, it is possible to measure the focal diameter of the X ray tube 8 by employing the method established in "JIS Z4704-1994, 7.4.1 FOCAL POINT TEST, (2.2) Slit Camera". Further, an X-ray irradiation time (exposure time) for completing every radiographing operation can be set at around several parts of one second, or two-three seconds at the longest.

In the present embodiment, a control device, detailed later, conducts an operation for changing the focal diameter of the X ray tube 8 from one to another by changing the angle of the target of the X ray tube. Various kinds of methods, such as a method for inclining the target, a method for providing the target having two angles in advance and changing the position of the target onto which the electron beam is irradiated, etc., can be employed for changing the angle of the target of the X ray tube. Other than the above, it is also possible that the system is so constituted that, for instance, the focal diameter of the X ray tube 8 is changed from one to another by changing the area of the electron beam to be irradiated onto the target, or plural X ray tubes, focal diameters of which are different from each other, are provided in the system, so as to change the X ray tube 8 itself from one to another at the time of the changeover operation between the Talbot interferometer method and Talbot-Lau interferometer method.

In this connection, it is preferable that the X ray tube 8 fulfills such a condition that the half-value width of the wavelength distribution of the X rays to be irradiated is equal to or smaller than 0.1 times of the peak wavelength of the X rays concerned. As far as the X ray tube 8 fulfills such the condition as abovementioned, the scope of the applicable X ray tube is not limited to the Coolidge X-ray tube or the rotation anode X-ray tube aforementioned, and the micro-focus X ray source or the like may be applicable as the X ray tube 8.

As shown in FIG. 3, the multi-slit element 11 is disposed at a lower side of the X ray tube 8. When the radiological image capturing apparatus 1 is used as the Talbot-Lau interferometer method, the multi-slit element 11 is inserted into the optical path of the X rays emitted from the X ray tube 8, while, when the radiological image capturing apparatus 1 is used as the Talbot interferometer method, the multi-slit element 11 is made to withdraw from the optical path concerned.

Figure 4:
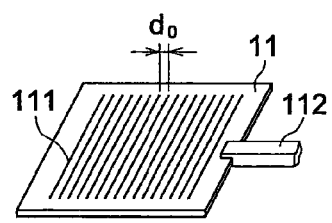
FIG. 4 shows a perspective view indicating a configuration of a multi-slit element.

As shown in FIG. 4, the multi-slit element 11 is constituted by plural thin plates, which are arranged so as to make a plurality of slits 111 line up in parallel to each other. Each of the plural thin plates is made of such a material that can shield the X rays (X ray absorbing capability is great), for instance, a lead, a tungsten, etc. Further, an aperture width of each of the slits 111 (namely, a slit width, so to speak) is set at a value in a range of 1-50 µm. In order to effectively utilize the Talbot effect and to acquire a sufficient amount of X rays, it is preferable that the slit width is formed at a value in a range of around 7-30 µm. Accordingly, the X rays that are incident onto the first diffraction grating, detailed later, are converted into the multi (plural) radiant sources while having the coherency property. In this connection, a space distance $d_0$ between the slits 111 of the multi-slit element 11 will be detailed later on.

Further, the slits 111 of the multi-slit element 11 are formed only within an area of the X-ray irradiation field of the X rays emitted from the X ray tube 8. As shown in FIG. 3, the multi-slit element 11 is supported by the supporting bar member 7 through a supporting member 112 in such a manner that the multi-slit element 11 can freely elevate and descend, and a position adjusting device 9 moves it upward or downward along the supporting bar member 7 so as to adjust the position of the multi-slit element 11.

In the present embodiment, the multi-slit element 11 is mounted onto the supporting bar member 7 in such a manner that the multi-slit element 11 is made to rotate around the axis of the supporting bar member 7 by the driving action of the position adjusting device 9. Accordingly, when the radiological image capturing apparatus 1 is used as the Talbot interferometer, the multi-slit element 11 is made to rotate around the axis of the supporting bar member 7 so as to withdraw from the optical path aforementioned. On the other hand, when the radiological image capturing apparatus 1 is used as the Talbot-Lau interferometer, the multi-slit element 11 is made to rotate around the axis of the supporting bar member 7 so as to insert it into the optical path aforementioned.

In this connection, it is also applicable that another driving device is employed for conducting the above-mentioned rotating action or the radiological image capturing apparatus 1 is so constituted that the abovementioned rotating action can be manually achieved. For instance, other than the above, it is also applicable that the coupling portion between the multi-slit element 11 and the supporting bar member 7 is configured as being capable of freely expanded and contracted, so that the multi-slit element 11 is inserted into or is made to withdraw from the optical path of the X rays by moving it toward the supporting bar member 7 or in a direction apart from the supporting bar member 7.

The multi-slit element 11 is disposed in such a manner that the extended directions of the slits 111 are parallel to those of diffraction members 152 of a first diffraction grating 15 detailed later. Further, as shown in FIG. 2, since the farther the X rays irradiated from the X ray tube 8 depart from the X ray tube 8, the wider the irradiation area of the X rays becomes, if the multi-slit element 11 is disposed at a position being far apart from the X ray tube 8, the area of the multi-slit element 11 should be widened, and possibly causes a physical interference with the subject H. In order to avoid the above inconveniences, it is preferable that the multi-slit element 11 is disposed at such a position that is apart from the focal point of the X ray tube 8 with a distance in a range of around 1-10 cm. In this connection, hereinafter, precisely speaking in the present invention, the distance between the X ray tube 8 and another member represents the distance between the focal point of the X ray tube 8 and another member.

A subject placing plate 12, on which the subject H is to be placed, is disposed at a position located below the X ray tube 8, in such a manner that the subject placing plate 12 is extended from the inner supporting shaft 5b of the supporting shaft 5 substantially in parallel to the floor surface. The subject placing plate 12 and the inner supporting shaft 5b are fixed neither to the image capturing main section 4 nor to the supporting bar member 7. Therefore, even if the image capturing main section 4 is driven to rotate clockwise or counterclockwise by the rotating action of the outer supporting cylinder 5a of the supporting shaft 5, the subject placing plate 12 does not rotate in conjunction with the rotating action of the outer supporting cylinder 5a.

The subject placing plate 12 can also rotate around the inner supporting shaft 5b, etc., as needed, and further, a pressing plate 13 presses the subject H onto the subject placing plate 12 so as to fix the subject H thereon, as needed. The pressing plate 13 is supported by the subject placing plate 12 through a supporting member (not shown in the drawings). It is applicable that the pressing plate 13 is made to move either automatically or manually.

As mentioned in the above, the subject placing plate 12 elevates and descends in conjunction with the up-and-down movements of the supporting base member 3 through the supporting shaft 5, for instance, so that the position of the subject placing plate 12 is adjusted at such a position that a patient can take an easy stance (natural posture) while putting his arm, serving as the subject H, on the subject placing plate 12. Further, a protector 14, which is extended in substantially a vertical direction, is mounted to the lower surface of the subject placing plate 12, so that the patient can take his position at the radiographing position without hitting his leg to a structure equipped under the subject placing plate 12 and without receiving X-ray exposure. In this connection, the pressing plate 13 and the protector 14 are not necessary indispensable structural elements, but it is applicable that the system can be configured without employing them.

The first diffraction grating 15 is disposed at a central section of the supporting bar member 7, located below the subject placing plate 12, in such a manner that the first diffraction grating 15 is made to freely elevate and descend, and a second diffraction grating 16 is disposed at a lower section of the supporting bar member 7, in such a manner that the second diffraction grating 16 is made to freely elevate and descend. The first diffraction grating 15 and the second diffraction grating 16 are held so as to arrange them in parallel to each other. The structures of the first diffraction grating 15 and the second diffraction grating 16, and positional relationships between an X-ray detector 17, detailed later, and them will be detailed later on.

As aforementioned, since the X rays irradiated from the X ray tube 8 are converted to the multi radiant sources by the multi-slit element 11, it is possible to regard the multi-slit element 11 as a radiant source. Further, it is necessary to appropriately adjust the distance between the first diffraction grating 15 and the radiant source. Accordingly, when the radiological image capturing apparatus 1 is used as the Talbot interferometer in which the first diffraction grating 15 is made to withdraw from the optical path of the X rays, the position adjusting device 9 makes the first diffraction grating 15 elevate and descend with respect to the supporting bar member 7 so as to adjust a distance L between the X ray tube 8 and the first diffraction grating 15. While, when the radiological image capturing apparatus 1 is used as the Talbot-Lau interferometer in which the first diffraction grating 15 is inserted into the optical path of the X rays, since the X rays irradiated from the X ray tube 8 are converted to the multi radiant sources by the multi-slit element 11, it is possible to regard the multi-slit element 11 as the radiant source, as aforementioned. Accordingly, the position adjusting device 9 makes the first diffraction grating 15 elevate and descend with respect to the supporting bar member 7, so as to adjust a distance L between the multi-slit element 11, serving as the radiant source, and the first diffraction grating 15.

Further, the position adjusting device 9 makes the second diffraction grating 16 elevate and descend with respect to the supporting bar member 7, so as to adjust a distance $Z_1$ between the first diffraction grating 15 and the second diffraction grating 16. In this connection, in the present embodiment, the position adjusting device 9 makes each of the first diffraction grating 15 and the second diffraction grating 16 elevate and descend independently from each other.

Figure 5:
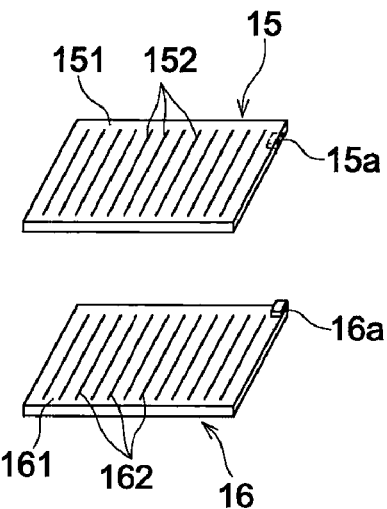
FIG. 5 shows perspective views of a first diffraction grating, a second diffraction grating and temperature sensors.

Further, for instance as shown in FIG. 5, a first temperature sensor 15a and a second temperature sensor 16a are mounted on the first diffraction grating 15 and the second diffraction grating 16 and disposed at such positions that cannot be captured as X-ray images, respectively. In this connection, for instance, it is applicable that sheets, which are made of material having a good thermal conductivity and does not impede the X-ray radiographing operation, are adhered onto the first diffraction grating 15 and the second diffraction grating 16, respectively, so as to keep the temperature uniform within the surface of each of them. Further, for instance, it is also applicable that Peltier elements, which are capable of conducting heating and cooling operations by controlling the direction and amplitude of electric currents flowing through them, are installed into the first diffraction grating 15 and the second diffraction grating 16, respectively, so as to make it possible to conduct the heating and cooling operations of them.

As shown in FIG. 2 and FIG. 3, a detector supporting plate 18 for supporting an X-ray detector 17 is supported at a lower section of the second diffraction grating 16, in such a manner that the X-ray detector 17 is made to freely elevate and descend with respect to the supporting bar member 7. Further, the position adjusting device 9 makes the detector supporting plate 18 elevate and descend independently from the first diffraction grating 15, etc., so as to adjust the position thereof.

The X-ray detector 17 is supported on the detector supporting plate 18 so as to oppose to the X ray tube 8. Although the X-ray detector 17 and the second diffraction grating 16 are depicted in the schematic diagrams shown in FIG. 2, FIG. 3, etc., in such a manner that some distance Z2 exists between them, in order to indicate that the X-ray detector 17 and the second diffraction grating 16 are separate elements, in reality, it is preferable that the X-ray detector 17 and the second diffraction grating 16 are disposed in such a state that both of them are in contact with each other. This is because, the farther the X-ray detector 17 departs from the second diffraction grating 16, the more the Moiré fringes become blurred. In other words, both of them are arranged so as to make the distance Z2 equal to substantially zero. In this connection, it is also applicable that the X-ray detector 17 and the second diffraction grating 16 are integrally structured as a single element. Further, in order to prevent a part of the human body, residing below the X-ray detector 17, from the X-ray exposure caused by the X rays emitted by the X ray tube 8, various kinds of radiation shielding members (not shown in the drawings) are disposed at the lower side of X-ray detector 17 and installed into the detector supporting plate 18, etc.

The X-ray detector 17 is constituted by a panel, a detector controlling section, etc. (not shown in the drawings), which are coupled to each other through a bus. Further, the X-ray detector 17 detects an amount of X rays penetrated through the subject H after emitted from the X ray tube 8, so as to output X-ray image data, representing the detected amount of X rays, to the image processing apparatus 30 through a network N.

It is preferable that a detector that employs any one of a FPD (Flat Panel Detector), a CR (Computed Radiography) and CCD (Charge Coupled Device), each of which output the amount of X rays as the digital information for every pixel, is used as the X-ray detector 17. Among them, the FPD, which is superior to the others as the two dimensional image sensor, is specifically preferable for this purpose. The overall size of the panel is selected as needed.

A distance $L_{total}$ between the X-ray detector 17 and the X ray tube 8 or the multi-slit element 11, serving as the radiant source, is set at such a value that is equal to or greater than 0.5 m. Further, considering the fact that the radiological image capturing apparatus 1 is used in a room environment and accuracy, strength, etc. of the radiological image capturing apparatus 1, the upper limit of the distance $L_{total}$ is set at around 2 m.

Figure 6:
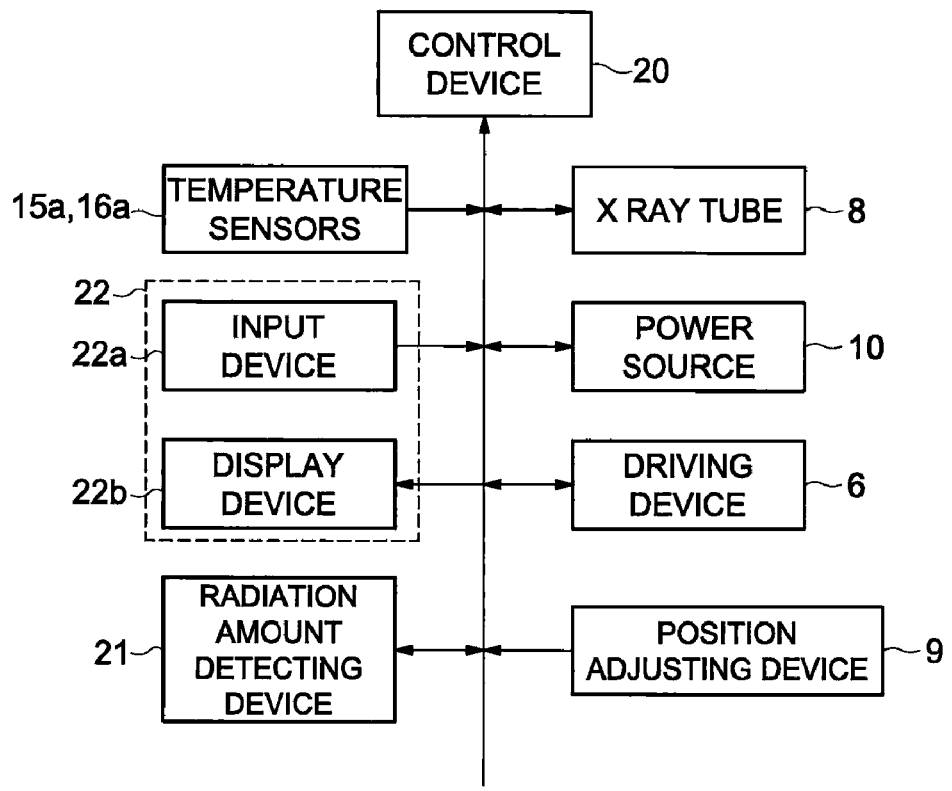
FIG. 6 shows a block diagram indicating a controlling configuration of a radiological image capturing apparatus, embodied in the present invention.

A control device 20, indicated in the schematic diagram shown in FIG. 6, conducts various kinds of setting operations and controlling operations for controlling actions to be conducted in the radiological image capturing apparatus 1. The control device 20 is provided with a computer constituted by a CPU (Central Processing Unit), a ROM (Read Only Memory), a RAM (Random Access Memory), etc., which are coupled to each other through a bus.

Although it is possible to install the control device 20 into the same room in which the radiological image capturing apparatus 1 is already installed, in the present embodiment, the control device 20 is constituted by employing a computer that is provided in the image processing apparatus 30 coupled to the radiological image capturing apparatus 1 through the network N. In other words, the control device 20 and the image processing apparatus 30 are constituted by employing the same computer. In this connection, it is also applicable that the control device 20 is constituted by employing another computer, which is equipped separately from the image processing apparatus 30 and which is coupled to the control device 20 through the network N.

As shown in FIG. 6, the control device 20 is coupled to the X ray tube 8, the power source 10, the driving device 6, the position adjusting device 9, the first temperature sensor 15*a* and the second diffraction grating 16, which are described in the foregoing. Other than the above, the control device 20 is also coupled to a radiation amount detecting device 21 to detect an amount of irradiated X rays, an operating device 22 that is provided with an input device 22*a* and a display device 22*b*, etc.

A controlling program for controlling various kinds of sections included in the radiological image capturing apparatus 1 and various kinds of processing programs are stored in a storage section of the control device 20, which includes the ROM, etc. Based on information inputted by the operator from the input device 22*a*, such as a keyboard, a mouse, a controller, etc., the control device 20 reads out the controlling program and the various kinds of processing programs from the storage section, so as to totally control operations to be conducted in the various kinds of sections included in the radiological image capturing apparatus 1, while making the display device 22*b*, such as a CRT display, a LCD (Liquid Crystal Display), etc., display contents of current controlling actions thereon.

For instance, when the operator inputs information for selecting any one of the Talbot interferometer method or Talbot-Lau interferometer method as a method to be currently employed in the radiological image capturing apparatus 1, and other information for setting the tube voltage to be currently applied for the X ray tube 8 as aforementioned, from the input device 22*a*, the average energy of the X rays to be irradiated from the X ray tube 8 is determined, and further, the distance L between the X ray tube 8 and the first diffraction grating 15 or the other distance L between the multi-slit element 11 serving as the radiant source and the first diffraction grating 15, and the distance $Z_1$ between the first diffraction grating 15 and the second diffraction grating 16 are also determined. Further, when the second diffraction grating 16 and the X-ray detector 17 are made to tightly contact with each other as aforementioned, assuming that the distance between the X ray tube 8 and the subject placing plate 12 is established as R1, and the other distance between the subject placing plate 12 and the X-ray detector 17 is established as R2, with respect to the schematic diagram shown in FIG. 2, the magnification factor of the subject H is determined by the following Equation, depending on the position of the subject placing plate 12.

$$(\text{magnification factor}) = (R1+R2)/R1$$

Accordingly, in the present embodiment, when the operator inputs the selected method to be currently employed, the tube voltage of the X ray tube 8, the distance L, the distance $Z_1$, etc., through the input device 22*a*, the control device 20 makes the position adjusting device 9 drive various kinds of sections, based on the inputted information, so as to conduct the operations for adjusting the positions of the X ray tube 8, the multi-slit element 11, the first diffraction grating 15, the second diffraction grating 16 and the X-ray detector 17. With respect to the multi-slit element 11, other than the position adjusting operation abovementioned, corresponding to the selected method currently established in the apparatus, the multi-slit element 11 is rotated around the axis of the supporting bar member 7 by the driving action of the position adjusting device 9 so as to insert it into the optical path of the X rays (in the case of the Talbot-Lau interferometer method), or to make it withdraw from the optical path (in the case of the Talbot interferometer method).

Successively, while maintaining the positional relationships of them, the positional adjusting operations are conducted by making the subject placing plate 12 elevate and descend in conjunction with the up and down movements of the supporting base member 3, so that the subject person can take a posture of being hardly fatigued.

In this connection, since the positional relationships should be adjusted so that the subject placing plate 12 and the first diffraction grating 15 are not in contact with each other, certain limitations are applied to the distances R1 and R2 aforementioned, and accordingly, a settable range of the magnification factor (=(R1+R2)/R1) is also limited. Accordingly, it is applicable that the radiological image capturing apparatus 1 is so constituted that the settable range of the magnification factor is displayed on the display device 22b at the time when the selected method to be currently employed, the tube voltage of the X ray tube 8, the distance L, the distance $Z_1$ and the magnification factor are inputted.

Further, it is also applicable that the radiological image capturing apparatus 1 is so constituted that an LUT (Look Up Table), in which the distances L and $Z_1$ being appropriate for the apparatus method and the tube voltage of the X ray tube 8 to be employed are stored, is provided in advance, so as to automatically set the distance L and the distance $Z_1$ at the time when the selected method to be currently employed and the tube voltage of the X ray tube 8 are inputted. In this case, when the selected method to be currently employed and the tube voltage of the X ray tube 8 are inputted, the operations for adjusting the positions of the X ray tube 8, the first diffraction grating 15, the second diffraction grating 16 and the X-ray detector 17 are automatically implemented, and further, when the magnification factor is inputted, the operations for adjusting the positional relationships between the subject placing plate 12 and them is implemented, corresponding to the above-inputted magnification factor.

Still further, although the radiological image capturing apparatus 1 embodied in the present invention is so constituted that, when the Talbot-Lau interferometer method is employed, the distance between the multi-slit element 11 disposed below the X ray tube 8 and the X ray tube 8 is set at a predetermined distance value, it is also applicable that the abovementioned distance is set at another value by inputting it at the same time when inputting the apparatus method and the tube voltage of the X ray tube 8 to be currently established in the apparatus, and/or an LUT for establishing a distance value, being optimum for the apparatus method and the tube voltage of the X ray tube 8 to be currently employed, is provided in advance.

Still further, as aforementioned, when any one of the Talbot interferometer method or the Talbot-Lau interferometer method is inputted as the selected apparatus method and the tube voltage of the X ray tube 8 is established, the control device 20 conducts the operation for changing the diameter of focal point of the X ray tube 8 corresponding to the selected apparatus method.

As abovementioned, the control device 20 activates the driving device 6 to rotate the supporting shaft 5 clockwise or counterclockwise, as shown in FIG. 3, so that the image capturing main section 4 is rotated around the subject H so as to adjust the radial-ray irradiation angle.

Further, when the radiological image capturing apparatus 1 is activated, the control device 20 irradiates the X rays emitted from the X ray tube 8 onto the subject H according to the electric power supplied from the power source 10 (in the case of the Talbot-Lau interferometer method, the X rays emitted from the multi radiant sources generated by the multi-slit element 11 are irradiated onto the subject H). Then, at the time when an amount of X rays detected by the radiation amount detecting device 21 reaches the predetermined amount of X rays, established in advance, the control device 20 stops the electric power currently supplied to the X ray tube 8 from the power source 10 so as to deactivates the X ray irradiating action. In this connection, the conditions for irradiating the X rays are established as needed by considering factors other than the amount of X rays detected by the radiation amount detecting device 21, namely, by taking a kind of the X-ray detector 17, etc. into account.

According to the present embodiment, since the control device 20 activates the driving device 6 to rotate the supporting shaft 5, so that the image capturing main section 4 is rotated around the subject H, so as to rotate the X ray tube 8, the first diffraction grating 15, the second diffraction grating 16 and the X-ray detector 17 (in the case of the Talbot-Lau interferometer method, the multi-slit element 11 is further added) around the subject H, it is possible to continuously capture X ray images by irradiating the X rays onto the subject H from plural directions. In this connection, the rotation amount of the image capturing main section 4 and an image capturing timing (corresponding to a rotated angle, at every which the X ray images are captured) are established by inputting them from the input device 22a.

Further, the control device 20 determines whether or not temperatures of the first diffraction grating 15 and the second diffraction grating 16, which are measured by the first temperature sensor 15a and the second temperature sensor 16a, respectively, are equal to or greater than the predetermined temperature established in advance. In the present embodiment, when at least one of the temperatures of the first diffraction grating 15 and the second diffraction grating 16 becomes equal to or greater than the predetermined temperature established in advance, a warning operation is conducted. The warning operation is achieved in such a manner that the control device 20 controls the display device 22b to display a kind of visual warning message thereon or to issue a kind of audible warning notification therefrom.

In this connection, in the case that the Peltier elements, which are capable of conducting heating and cooling operations by controlling the directions and amplitudes of electric currents flowing through them, are installed into the first diffraction grating 15 and the second diffraction grating 16, respectively, as aforementioned, when the temperatures of the first diffraction grating 15 and the second diffraction grating 16, which are measured by the first temperature sensor 15a and the second temperature sensor 16a, are increase or decrease, it is possible to activate the Peltier elements so as to control the temperatures of the first diffraction grating 15 and the second diffraction grating 16 to be kept within a predetermined temperature range.

Further, as detailed later, the radiological image capturing apparatus 1 embodied in the present invention is so constituted that the control device 20 can determine whether or not a distortion due to the temperature change or another distortion due to the change over time has generated on the first diffraction grating 15 or the second diffraction grating 16, based on an image of the Moiré fringes detected in such a state that the subject H is not placed on the subject placing plate 12 (refer to Moiré fringes M indicated in the schematic diagram shown in FIG. 7, detailed later).

Concretely speaking, at the time stage when the radiological image capturing apparatus 1 is installed into a certain room after shipped from a factory, or when the first diffraction grating 15 and/or the second diffraction grating 16 are/is replaced with a new one, the control device 20 stores an image of the Moiré fringes, which is captured in the state that the subject H is not placed on the subject placing plate 12 before the apparatus is put in its actual operation, into the storage section including a RAM, etc. After that, at the next time stage when a predetermined condition established in advance, such as a condition that the operating time of the radiological image capturing apparatus 1, established in advance, has elapsed, a condition that a number of X ray irradiation times has reached to a predetermined number of times, etc., is fulfilled, the control device 20 newly conducts the operation for capturing an image of the Moiré fringes in the state that the subject H is not placed on the subject placing plate 12. Otherwise, it is also applicable that the apparatus is so constituted that the control device 20 periodically conducts the operation for capturing an image of the Moiré fringes.

Successively, the control device 20 reads out the image of the Moiré fringes, captured and stored before the apparatus is put in its actual operation, from the storage section, to compare it with the other image of the Moiré fringes currently captured at this time. As a result of the abovementioned comparison, when the currently-captured image of the Moiré fringes fulfills at least one of the conditions that: an interval of the Moiré fringes in the currently-captured image is expanded or reduced at a value equal to or greater than a predetermined value, compared to that in the image of the Moiré fringes captured and stored before the apparatus is put in its actual operation; a part of or all of the Moiré fringes are curved; a difference between a maximum part and a minimum part of detected amount of the irradiated X rays among the Moiré fringes is expanded or reduced at a value equal to or greater than a predetermined value; etc., the control device 20 determines that a distortion (deformation) has generated in the diffraction member(s) (grating) of the first diffraction grating 15 and/or the second diffraction grating 16. In this connection, it is applicable that the abovementioned operation is conducted in any one of the Talbot interferometer method and the Talbot-Lau interferometer method, or in both methods.

When determining that a distortion (deformation) has generated in the diffraction member(s) of the first diffraction grating 15 and/or the second diffraction grating 16 as abovementioned, the control device 20 controls the display device 22b to display a kind of visual warning message thereon or to issue a kind of audible warning notification therefrom.

Further, in the present embodiment, the apparatus is so constituted that the control device 20 detects an abnormal shadow candidate from the captured X-ray image. Further, the apparatus is so constituted that, when detecting the abnormal shadow candidate, the control device 20 changes the apparatus method from the Talbot-Lau interferometer method to the Talbot interferometer so as to capture the abnormal shadow candidate being sharper than ever.

The operation for detecting the abnormal shadow candidate from the captured X-ray image can be conducted by employing, for instance, the technology of the medical image diagnosis assisting system, set forth in Tokkai 2005-102936, which has been previously submitted by the applicant of the present invention. In this system, an image analysis processing is applied to the medical image, such as an X-ray image, etc., so as to extract its featuring amount, and then, based on the extracted featuring amount, an abnormal shadow candidate is detected from the image concerned.

In this connection, it is applicable that the system is so constituted that the abovementioned apparatus that detects the abnormal shadow candidate from the X-ray image, captured by the radiological image capturing apparatus 1, is installed as the diagnosis assisting apparatus (not shown in the drawings) separately from the radiological image capturing apparatus 1, and is coupled to the radiological image capturing apparatus 1, etc. through the network N, so as to provide it within the radiological image capturing system 100.

For instance, it is also applicable that the system is so constituted that, when the diagnosis assisting apparatus detects an abnormal shadow candidate and transmits information in regard to the detected abnormal shadow candidate, the control device 20 of the radiological image capturing apparatus 1 changes the method to be employed in the radiological image capturing apparatus 1 from the Talbot-Lau interferometer method to the Talbot interferometer method, based on the information sent from the diagnosis assisting apparatus.

As shown in FIG. 1, the image processing apparatus 30 and the image outputting apparatus 50 are coupled to the radiological image capturing apparatus 1 through the network N. The image outputting apparatus 50 includes: a display device, such as a CRT display, a LCD (Liquid Crystal Display), etc.; a developing device for outputting an image onto a film; etc.

Receiving X-ray image data for every captured image sent from the X-ray detector 17 of the radiological image capturing apparatus 1 through the network N, the image processing apparatus 30 temporarily stores the received X-ray image data into a storage section (not shown in the drawings). In this connection, at least one of an HDD (Hard Disc Drive) serving as a high-speed accessible mass memory, an HDD Array, such as a RAID (Redundant Array of Independent Disks), etc., a silicone disc, etc. can be employed as the storage section.

Further, the image processing apparatus 30 makes the radiological image capturing apparatus 1 capture an image of the Moiré fringes, and then, transmit X-ray image data of the image, so as to store the X-ray image data into storage section. This X-ray image data is temporarily established as the reference X-ray image data. After that, when the radiological image capturing apparatus 1 commences the operation for capturing an X-ray image of the subject H, the image processing apparatus 30 corrects the transmitted X-ray image data representing the image that is captured by the radiological image capturing apparatus 1 in a state that the subject H is present, based on the reference X-ray image data.

The correcting operation is conducted with respect to, for instance, a positional deviation on the image, sensitivity unevenness (namely, non-uniformity in the signal values detected by the detector), etc. Concretely speaking, when it is recognized in advance from the reference X-ray image data that a positional deviation is generated in a fixed pixel area on the image, it is possible to correct the positional deviation by conducting such the correcting operation that turns the fixed pixel area, existing in the image represented by the transmitted X-ray image data, back to the original position by an amount of the positional deviation. Further, by dividing the X-ray image data, the positional deviation of which has been corrected, by the reference X-ray image data, for every pixel, it is possible to acquire an X-ray image having no sensitivity non-uniformity to be caused by the existence of the diffraction grating. The image processing apparatus 30 also stores the above-processed X-ray image data into the storage section.

Still further, it is possible for the image processing apparatus 30 not only to convert the X-ray image (the image of the Moiré fringes) detected by the X-ray detector 17 to a distribution image of angles at which the X rays are curved by the refraction effect caused by the subject H (phase shift differential image), but also to obtain such an image that represents the phase sift itself, acquired by integrating the phase shift differential image. The well-known methods, such as the method set forth in the International Publication 2004/058070, etc., are employed for the conversion processing and the image acquisition processing, both above-mentioned.

Yet further, in the present embodiment, when receiving plural X-ray image data sets, which represent a plurality of X-ray images continuously captured by changing the direction for radiographing the subject H and are sent from the radiological image capturing apparatus 1, the image processing apparatus 30 creates a three dimensional image of the subject H, based on the above-received plural X-ray image data sets. The image outputting apparatus 50 displays the created three-dimensional image on the LCD, etc., or outputs it onto a film, etc., so as to output the three dimensional image created in the above. In this connection, a certain well-known method can be employed as the method for creating the three dimensional image from the plurality of two-dimensional images acquired by capturing the subject H from the various directions.

In this connection, it is also possible to further apply another kind of processing to the plurality of two-dimensional images and/or the three dimensional image, which are/is acquired through the abovementioned processes. For instance, it becomes possible to acquire such the image, etc., that is displayed on the screen or outputted on the film, in such a manner that the brightness of the image, in which the concerned cartilage section is represented with the deep color in contrast to the pale color of the background, is reversed, or in such a manner that the considerably changed portion, compared to the standard model of the cartilage section, is colored, etc. Further, when a manifestation of the rheumatic disease emerges on the finger, it becomes possible to observe the diseased part as if it were a moving image, by acquiring a plurality of three-dimensional images in which the bending angles of the finger joints are varied in various kinds of directions.

In this connection, it is applicable that the abovementioned operations are implemented in any one of the Talbot interferometer method and the Talbot-Lau interferometer method, or in both of them.

Next, the Talbot-Lau interferometer to be configured in the radiological image capturing apparatus 1, embodied in the present invention, will be detailed in the following.

Further, the functions of the radiological image capturing apparatus 1 will be detailed in the following, in conjunction with the explanations of the configurations of the multi-slit element 11, the first diffraction grating 15 and the second diffraction grating 16, and the explanations of the positional relationships between the X-ray detector 17 and them.

Figure 7:
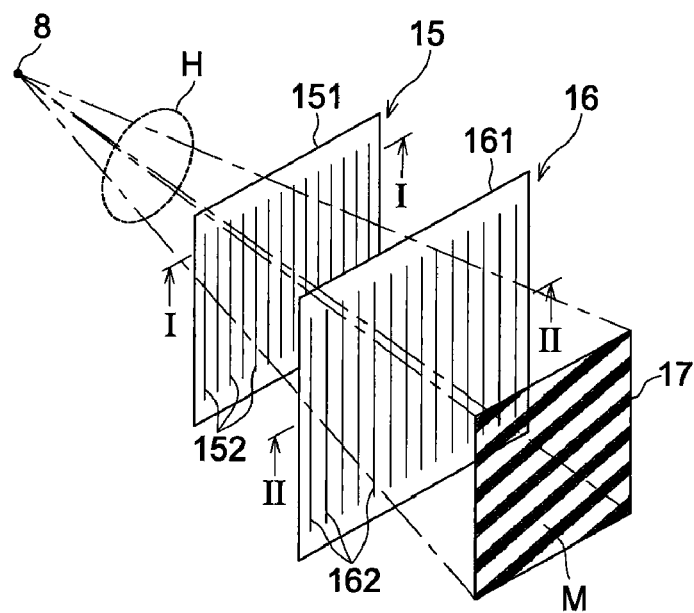
FIG. 7 shows a perspective view of a main part for explaining penetrating actions of X rays and Moiré stripes when a radiological image capturing apparatus is used in a Talbot interferometer method.
Figure 8:
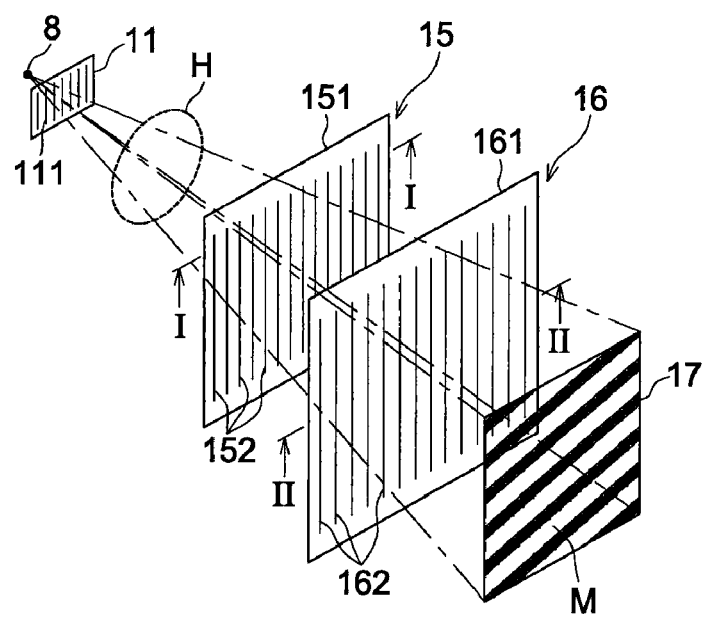
FIG. 8 shows a perspective view of a main part for explaining penetrating actions of X rays and Moiré stripes when a radiological image capturing apparatus is used in a Talbot-Lau interferometer method.

As shown in FIG. 7 and FIG. 8, in the present embodiment, the X rays irradiated from the X ray tube 8 penetrate through the multi-slit element 11 in the case of the schematic diagram shown in FIG. 8, and successively penetrate through the subject H, and then, penetrate through the first diffraction grating 15 and the second diffraction grating 16, and finally, are incident onto the X-ray detector 17. As shown in FIG. 7, the Talbot interferometer is constituted by the X ray tube 8, the first diffraction grating 15 and the second diffraction grating 16, while, as shown in FIG. 8, the Talbot-Lau interferometer is constituted by the X ray tube 8, the multi-slit element 11, the first diffraction grating 15 and the second diffraction grating 16.

Figure 9:
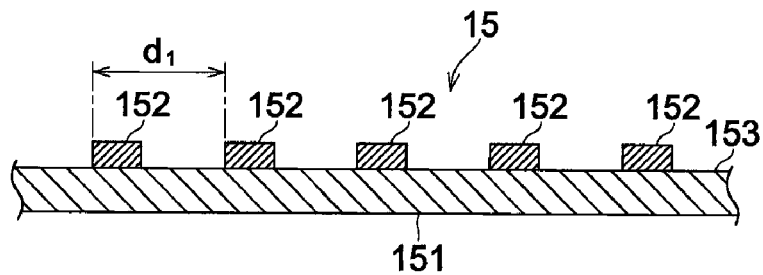
FIG. 9 shows a cross sectional view at an I-I position shown in FIG. 7.

FIG. 9 shows a cross sectional schematic diagram at the I-I cross section indicated in the schematic diagrams shown in FIG. 7 and FIG. 8. As shown in FIG. 7 through FIG. 9, the first diffraction grating 15 is provided with a substrate 151 and a plurality of the diffraction members 152 that are arranged on the substrate 151, so as to yield a Talbot effect, detailed later, by diffracting the X rays that penetrate through the subject placing plate 12 and the subject H, held by the subject placing plate 12, and are irradiated thereon. The substrate 151 is made of, for instance, a glass material or the like. In this connection, a surface of the substrate 151, on which the diffraction members 152 are arranged, is referred to as a diffraction grating surface 153.

Each of the diffraction members 152 is such a linear member that is extended in a direction orthogonal to the irradiation direction of the X rays irradiated from the X ray tube 8, namely, for instance, that is extended in a up-down direction of the schematic diagrams shown in FIG. 7 and FIG. 8. The thicknesses of the diffraction members 152 are substantially the same, for instance, each of them is formed in a range of 10-50 µm.

Further, as shown in FIG. 9, an interval distance $d_1$, being one of relative distances between the plural diffraction members 152, is set at a fixed value, and the relative distances between the diffraction members 152 are substantially the same. The interval distance $d_1$ is formed at a value in a range of around 3-10 µm. The interval distance $d_1$ is also referred to as a grating period or a grating interval. In this connection, both the range of the interval distance $d_1$ in the plural diffraction members 152 and the other range of the width of each of the diffraction members 152 are not limited specifically. It is applicable that the diffraction members 152 are formed in such a manner that the interval distance between the diffraction members and the width of each of the diffraction members are either the same as each other or different from each other.

It is preferable that a material to be employed for structuring the diffraction members 152 is superior in the X rays absorbing property, and, for instance, a metallic material, such as a gold, a silver, a platinum, etc., can be employed for this purpose. The diffraction members 152 are formed on the substrate 151, for instance, by plating or vapor-depositing the abovementioned metal thereon. The diffraction members 152 is such a member that changes the phase velocity of the X rays irradiated onto the diffraction members 152, and it is preferable that the diffraction members 152 is such a member that structures, so called, the phase-type diffraction grating, which yields a phase modulation at an angle in a range of about 80°-100°, preferably at 90°. The X rays are not necessary a single color, but it is applicable that the X rays have such an energy width (namely, a wavelength spectral width) that fulfils the abovementioned conditions.

Figure 10:
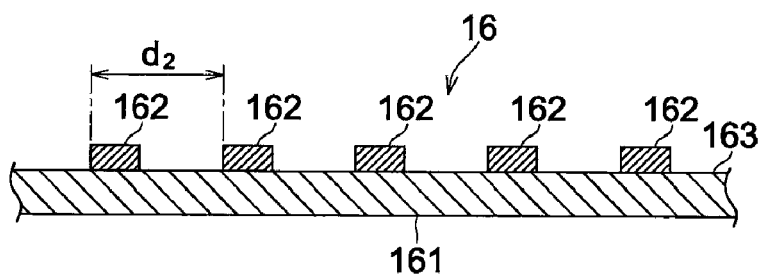
FIG. 10 shows a cross sectional view at an II-II position shown in FIG. 7.

FIG. 10 shows a cross sectional schematic diagram at the II-II cross section indicated in the schematic diagrams shown in FIG. 7 and FIG. 8. As shown in FIG. 7, FIG. 8 and FIG. 10, the second diffraction grating 16 is provided with a substrate 161 and a plurality of diffraction members 162 in the same manner as those of the first diffraction grating 15. In this connection, a surface of the substrate 161, on which the diffraction members 162 are arranged, is referred to as a diffraction grating surface 163.

Wherein, an interval distance $d_2$, being one of relative distances between the plural diffraction members 162, is set at such a value that the ratio of the distance $(L+Z_1)$ from the X ray tube 8 to the second diffraction grating 16 and the interval distance $d_2$ is substantially equal to the other ratio of the distance L from the X ray tube 8 to the first diffraction grating 15 and the interval distance $d_1$. In this connection, for instance, it is also possible to set the interval distance $d_2$, being one of relative distances between the plural diffraction members 162 of the second diffraction grating 16, at such a value that is substantially the same as the interval distance $d_1$, being one of relative distances between the plural diffraction members 152 of the first diffraction grating 15. Further, the width of each of the diffraction members 162 of the second diffraction grating 16 is substantially the same as the width of each of the diffraction members 152 of the first diffraction grating 15.

As detailed later, the second diffraction grating 16 is disposed in such a state that the extended direction of the diffraction members 162 is rotated relative to the other extended direction of diffraction members 152 of the first diffraction grating 15 by a minute angle θ, so as to form an image contrast by diffracting the X rays previously diffracted by the first diffraction grating 15. Although it is desirable that the second diffraction grating 16 is an amplitude-type diffraction grating in which the diffraction members 162 are made to be thicker than ever, it is also possible to employ such a structure that is similar to that of the first diffraction grating 15.

Figure 11:
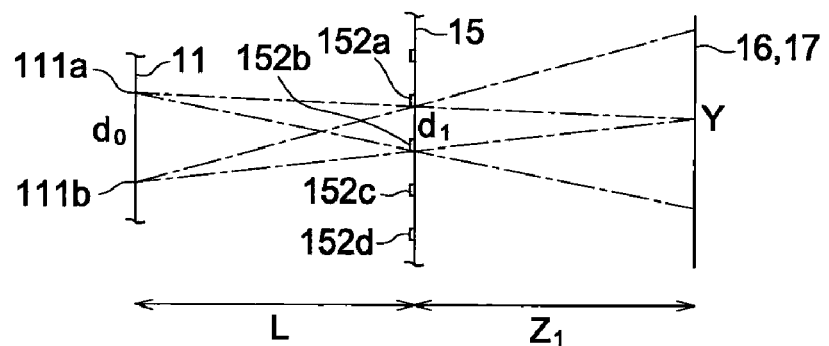
FIG. 11 shows a schematic diagram for explaining such a state that a self-image of a first diffraction grating, which is formed by X rays passing through each of slits of a multi-slit element, is just in focus on a second diffraction grating.

Next, the structure of the multi-slit element 11 will be detailed in the following. As shown in FIG. 11, when the radiological image capturing apparatus 1 is used as the Talbot-Lau interferometer method, the multi-slit element 11 and the first diffraction grating 15 are apart from each other by the distance L. Further, for instance as detailed later, an X ray passing through a slit 111a, serving as one of the multi-slits of the multi-slit element 11, forms self-images of a diffraction member 152a and a diffraction member 152b of the first diffraction grating 15 on the second diffraction grating 16, which is disposed at the position being apart from the first diffraction grating 15 by the distance $Z_1$, (namely, on the X-ray detector 17 that is closely adjacent to the second diffraction grating 16).

Further, another X ray passing through a slit 111b that is located at position adjacent to the slit 111a also forms self-images of a diffraction member 152a and a diffraction member 152b of the first diffraction grating 15 on the second diffraction grating 16, respectively. In other words, each of the X rays passing through each of the slits 111 of the multi-slit element 11 forms each of self-images of the diffraction members 152 on the second diffraction grating 16, resulting in a striped pattern of the self-images.

On that occasion, unless a slit interval distance $d_0$ between the slits 111 of the multi-slit element 11 is appropriate, the self-images in the striped pattern, which are formed by the X rays passing through the slit 111a and the slit 111b of the multi-slit element 11, counteract with each other.

However, if the slit interval distance $d_0$ is adjusted, so as to make the self-image of the diffraction member 152a, formed by the X ray passing through the slit 111a, and the other self-image of the diffraction member 152b, formed by the X ray passing through the slit 111b, overlap with each other at a position Y on the second diffraction grating 16, the self-image and the other self-image in the striped pattern can be superimposed with each other, resulting in achievement of an in-focus state.

In the above case, the slit interval distance $d_0$ between the slits 111 of the multi-slit element 11, the interval distance (grating period) $d_1$, being one of relative distances between the plural diffraction members 152 of the first diffraction grating 15, the distance L between the multi-slit element 11 and the first diffraction grating 15 and the distance $Z_1$ from the first diffraction grating 15 to the second diffraction grating 16, fulfill the Equation indicated as follow.

$$d_0 : d_1 = (L+Z_1) : Z_1 \quad (1)$$

Deriving from the Equation (1), the slit interval distance $d_0$ can be represented by the Equation (2) indicated as follow.

$$d_0 = \frac{L+Z_1}{Z_1} d_1 \quad (2)$$

Further, referring to FIG. 11, although there has been considered such the case that the X rays, passing through the slit 111a and the slit 111b, further pass through the portions of the diffraction member 152a and the diffraction member 152b, which are adjacent to each other on the first diffraction grating 15, for instance, even if the X rays pass through the portions of the diffraction member 152a and the diffraction member 152c or the diffraction member 152d, each of which resides at a position being apart from the diffraction member 152a by an integral multiple of the grating period $d_1$, namely, even when the Equation (3), which is indicated as follow and in which "$d_1$" in the Equation (2) is substituted by "$pd_1$" acquired by multiplying "$d_1$" by "p", is fulfilled, the self-images in the striped pattern formed on the first diffraction grating 15 are just superimposed with each other, resulting in achievement of the in-focus state.

$$d_0 = \frac{L+Z_1}{Z_1} pd_1 \quad (3)$$

Still further, since the Equation of $L+Z_1+Z_2=L_{total}$ has been established as aforementioned, and the distance $Z_2$ between the second diffraction grating 16 and the X-ray detector 17 are approximately zero, the Equation (3) can be also expressed by the Equation (4) indicated as follow.

$$d_0 = \frac{L_{total}}{Z_1} pd_1 \quad (4)$$

In other words, if the slits 111 of the multi-slit element 11 are appropriately formed in such a manner that the slit interval distance $d_0$ of the slits 111 fulfills the Equation (3) and the Equation (4), the X rays respectively passing through the slits 111 of the multi-slit element 11 effectively form the self-images of the first diffraction grating 15 on the second diffraction grating 16 so as to make the self-images overlap each other, and as a result, it becomes possible to acquire the self-images being in-focus.

Next, when the radiological image capturing apparatus 1 is used in either the Talbot interferometer method or Talbot-Lau interferometer method, the conditions that the X ray tube 8, the multi-slit element 11, the first diffraction grating 15 and the second diffraction grating 16 constitute the interferometer, will be detailed in the following.

Initially, when the radiological image capturing apparatus 1 is used in the Talbot interferometer method, the conditions that the X ray tube 8, the first diffraction grating 15 and the second diffraction grating 16 constitute the interferometer will be detailed in the following.

On the premise that the first diffraction grating 15 is the phase-type diffraction grating, the distance $Z_1$ between the first diffraction grating 15 and the second diffraction grating 16 should fulfill the condition indicated as follow. In this connection, "m" represents an integer number and "$d_1$" represents the interval distance, being one of relative distances between the plural diffraction members 152 of the first diffraction grating 15, as aforementioned.

$$Z_1 = \left(m + \frac{1}{2}\right)\frac{d_1^2}{\lambda} \quad (5)$$

Figure 12:
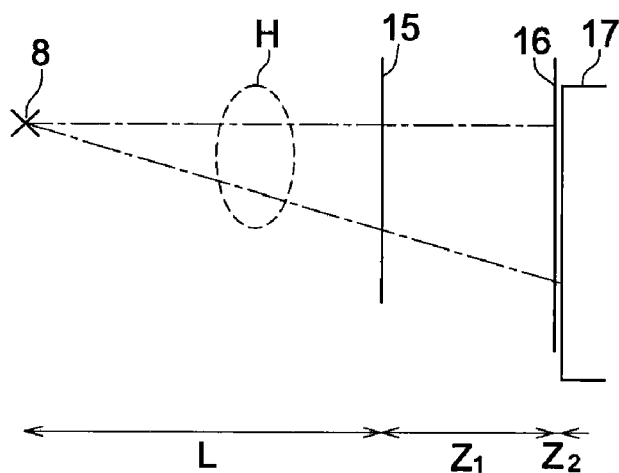
FIG. 12 shows an explanatory schematic diagram for explaining a positional relationship between a X ray tube, a subject H, a first diffraction grating, a second diffraction grating and an X-ray detector, in a radiological image capturing apparatus employing the Talbot interferometer method.

Explaining the Talbot effect while referring to the schematic diagram shown in FIG. 12, in the case that the first diffraction grating 15 is the phase-type diffraction grating, when the plane wave of the X ray passes through the first diffraction grating 15, the Talbot effect is to form the self-image of the diffraction grating at the distance given by the Equation (5). In the state that the subject H is absence, the self-image of the first diffraction grating 15, namely, the image of diffraction members 152 in which the grating period for every interval distance $d_1$ is slightly expanded, emerges at such a position that is apart from the first diffraction grating 15 by the distance $Z_1$ given by the Equation (5).

In this connection, at a position other that the position of the distance $Z_1$ given by the Equation (5), the self-image cannot be observed or may be out of focus. However, in the vicinity of the position of the distance $Z_1$ given by the Equation (5), the relatively in-focus state of the self-image is maintained. Accordingly, the distance $Z_1$ defined by Equation (5) includes allowable distances in the vicinity of the distance $Z_1$. Further, when setting the actual distance $Z_1$, some allowance for the distance $Z_1$ given by the Equation (5) can be introduced into a distance to be actually set.

Then, when the second diffraction grating 16 is positioned at a position of the distance $Z_1$ in such a state that the extended direction of the diffraction members 162 is rotated relative to the other extended direction of diffraction members 152 of the first diffraction grating 15 by a minute angle θ, Moiré fringes emerge, and the X-ray detector 17 detects a Moiré stripe image M, which is formed by projecting the Moiré fringes, as shown in FIG. 7. In this case, an interval distance between the Moiré stripes of the Moiré stripe image M, generated in the above, is given by $d_1/\theta$, from the interval distance $d_1$ of the diffraction members 152 and the minute angle θ.

On the other hand, when the subject H exists between the X ray tube 8 and the first diffraction grating 15, the phase of the X rays emitted from the X ray tube 8 would shift in mid course of passing through the subject H. This phase sift causes a distortion of the wave front of the X rays being incident into the first diffraction grating 15. Accordingly, the self-image of the first diffraction grating 15 is deformed, depending on the distortion of the wave front.

Successively, when the X rays diffracted by the first diffraction grating 15 passes through the second diffraction grating 16, the Moiré stripe image M is distorted according to the distortion of the wave front of the X rays, namely, according to the shape of the subject H. On that occasion, since the X rays penetrate through the inside section of the subject H, the X rays would be distorted by the shape of the inside section, and accordingly, those distortions will be projected into the Moiré stripe image M.

On that occasion, actually, the self-image of the first diffraction grating 15 is also reflected by the distortion caused by the subject H, and accordingly, at the position of the distance $Z_1$ given by the Equation (5), it emerges such a state that the shape of the subject H and the shape of its inner section are reflected into the diffraction stripe of the diffraction members 152 in which the grating period for every interval distance $d_1$ is slightly expanded. However, it has been virtually impossible for the normal-type X-ray detector 17 to detect the diffraction stripe above-mentioned with its resolution capability. Accordingly, since it is also impossible to detect the distortion caused by the subject H, it has been difficult to obtain the X ray image of the subject H as it is.

However, if the apparatus is so constituted that the second diffraction grating 16 is rotated relative to first diffraction grating 15 by a minute angle θ so as to form such a Moiré stripe image in which the interval distance between the stripes is far greater than the grating period, it becomes possible for the normal-type X-ray detector 17 to detect the diffraction stripe abovementioned even with its resolution capability. Further, by employing the normal-type X-ray detector 17 for detecting the Moiré stripe image M distorted according to the shape of the subject H and the shape of its inner section, it becomes possible to obtain the X ray image of the subject H, into which the shape of the subject H and the shape of its inner section are projected.

In the radiological image capturing apparatus 1 employing the Talbot interferometer, embodied in the present invention, as described in the foregoing, in order to heighten the coherence property of X rays emitted from the X ray tube 8 and having an average energy in a range of 15-60 keV, as aforementioned, at the time when the concerned X rays are incident into the first diffraction grating 15, it is necessary to set the distance L between the X ray tube 8 and the first diffraction grating 15 at a value equal to or greater that a certain fixed distance.

As aforementioned, when the radiological image capturing apparatus 1 is used as the Talbot interferometer method, a focal point diameter "a" is set at a value equal to or greater that 1 μm. When the focal point diameter "a" is set at 1 μm as its minimum value and the average energy of the X rays is set at 60 keV as its maximum value, it is necessary to set the distance L between the X ray tube 8 and the first diffraction grating 15 at a value equal to or greater that 0.5 m. However, since the coherency (coherency distance) is in proportion to the distance L while in inverse proportion to the average energy of the X rays and the focal point diameter, in the case that the coherency is acquired at 60 keV of the X ray average energy, for instance, the distance L between the X ray tube 8 and the first diffraction grating 15 can be set at a value equal to or greater than 0.125 m (12.5 cm) as far as the average energy of the X rays is 15 keV, or, even if the focal point diameter "a" of the X ray tube 8 is widened up to 4 μm, the equivalent degree of the coherency can be obtained.

Further, although the distance $Z_1$ between the first diffraction grating 15 and the second diffraction grating 16 is given by the Equation (5) aforementioned, as being recognizable from the fact that the Equation (5) includes the wavelength λ, the distance $Z_1$ depends on the average energy of the X rays. Accordingly, as aforementioned, when the interval distance $d_1$, being one of relative distances between the plural diffraction members 152 of first diffraction grating 15, is set at around 3 μm, which is technically formable value, and the average energy of the X rays to be irradiated is set at a value in a range of 15-60 keV, it is necessary to set the distance $Z_1$ at a value equal to or greater than 0.05 m.

In this connection, the lower limit of the range of a value, which is settable as the distance $L_{total}$ from X ray tube 8 to the X-ray detector 17, is specified by the limitations for the distance L and the distance $Z_1$ (the distance $Z_2$ from second diffraction grating 16 to the X-ray detector 17 is zero). Further, although its upper limit is not limited to a specific value, considering the fact that the radiological image capturing apparatus 1, embodied in the present invention, would be virtually used in the room environment, the upper limit may be set at around 2 meters.

Next, when the radiological image capturing apparatus 1 is used in the Talbot-Lau interferometer method, the conditions that the X ray tube 8, the multi-slit element 11, the first diffraction grating 15 and the second diffraction grating 16 constitute the interferometer will be detailed in the following.

Figure 13:
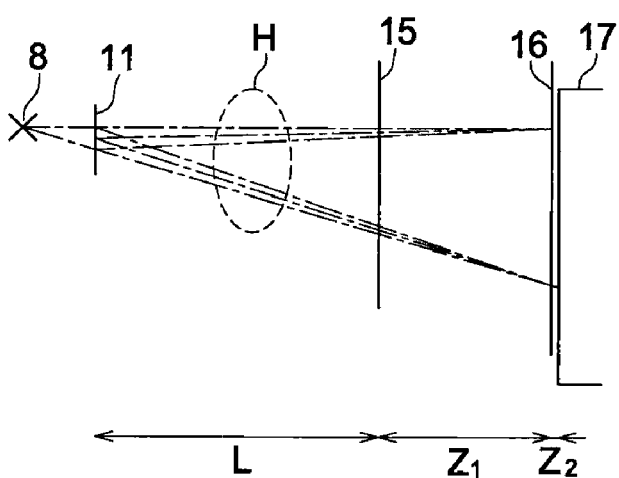
FIG. 13 shows an explanatory schematic diagram for explaining a positional relationship between a X ray tube, a multi-slit element, a subject H, a first diffraction grating, a second diffraction grating and an X-ray detector, in a radiological image capturing apparatus employing the Talbot-Lau interferometer method.

Even in this case, the conditions are principally similar to those of the Talbot interferometer method abovementioned, the distance $Z_1$ between the first diffraction grating 15 and the second diffraction grating 16 is set at such a value that fulfills the Equation (5) aforementioned. Further, as shown in FIG. 13, each of the X rays passing through each of the slits 111 of the multi-slit element 11 yields the Talbot effect aforementioned. Then, each of the X rays passing through each of the slits 111 forms the self-image of the first diffraction grating 15 at the position being apart from the first diffraction grating 15 by the distance $Z_1$. On that occasion, if the slit interval distance $d_0$ is structured so as to fulfill the Equation (3) and the Equation (4), the self-images just overlap with each other at the position being apart from the first diffraction grating 15 by the distance $Z_1$, resulting in a just in-focus state.

Accordingly, when the second diffraction grating 16 is positioned at a position of the distance $Z_1$ in such a state that the extended direction of the diffraction members 162 is rotated relative to the other extended direction of diffraction members 152 of the first diffraction grating 15 by a minute angle θ, Moiré fringes emerge, and the X-ray detector 17 detects the Moiré stripe image M, which is formed by projecting the Moiré fringes, as shown in FIG. 8.

On the other hand, when the subject H exists between the multi-slit element 11 and the first diffraction grating 15, the phase of each of the X rays, emitted from the X ray tube 8 and passing through the multi-slit element 11, would shift in mid course of passing through the subject H. This phase sift causes a distortion of the wave front of each of the X rays being incident into the first diffraction grating 15. Accordingly, the self-image of the first diffraction grating 15 is deformed, depending on the distortion of the wave front.

Successively, when each of the X rays diffracted by the first diffraction grating 15 passes through the second diffraction grating 16, the Moiré stripe image M is distorted according to the distortion of the wave front of each of the X rays, namely, according to the shape of the subject H. On that occasion, since each of the X rays penetrates through the inside section of the subject H, each of the X rays would be distorted by the shape of the inside section, and accordingly, those distortions will be projected into the Moiré stripe image M. As described in the above, by employing the normal-type X-ray detector 17 for detecting the Moiré stripe image M distorted according to the shape of the subject H and the shape of its inner section, it becomes possible to obtain the X ray image of the subject H, into which the shape of the subject H and the shape of its inner section are projected.

In the case that the Talbot-Lau interferometer method as abovementioned is employed, when a width of aperture of each of the slits 111 of the multi-slit element 11, corresponding to the focal point diameter of the X ray tube 8, is set at 1 μm as its minimum value and the average energy of the X rays is set at 60 keV as its maximum value, it is necessary to set the distance L between the multi-slit element 11 and the first diffraction grating 15 at a value equal to or greater that 0.5 m. However, since the coherency (coherency distance) is in proportion to the distance L while in inverse proportion to the average energy of the X rays and the width of aperture of each of the slits 111, in the case that the coherency is acquired at 60 keV of the X ray average energy, for instance, the distance L between the multi-slit element 11 and the first diffraction grating 15 can be set at a value equal to or greater than 0.125 m (12.5 cm) as far as the average energy of the X rays is 15 keV, or, even if the width of aperture of each of the slits 111 is widened up to 4 μm, the equivalent degree of the coherency can be obtained.

As well as in the case of the Talbot interferometer method, it is necessary in the Talbot-Lau interferometer method to set the distance $Z_1$ between first diffraction grating 15 and the second diffraction grating 16 at a value equal to or greater than 0.05 m.

Further, the slit interval distance $d_0$ of the multi-slit element 11 has the relationship, represented by the aforementioned Equation (2), with respect to the interval distance (grating period) $d_1$, being one of relative distances between the plural diffraction members 152 of the first diffraction grating 15, the distance L between the multi-slit element 11 and the first diffraction grating 15, and the distance $Z_1$ between first diffraction grating 15 and the second diffraction grating 16. Accordingly, when the abovementioned limitations are applied to the interval distance (grating period) $d_1$, the distance L, the distance $Z_1$ and further, the slit width, the slit interval distance $d_0$ is set at a value equal to or greater than 2 μm as its setting range.

As described in the foregoing, various kinds of setting conditions are different from each other between in the case that the radiological image capturing apparatus 1 is used as the Talbot interferometer method and in the other case as the Talbot-Lau interferometer method. Accordingly, for instance as aforementioned, when detecting an abnormal shadow candidate from the captured X ray image, or when receiving the information in regard to an abnormal shadow candidate detected and transmitted by the diagnosis assistance apparatus of the radiological image capturing system 100, the control device 20 changes the Talbot-Lau interferometer method, shown in FIG. 2 and FIG. 3, to the Talbot interferometer method, in order to capture the abnormal shadow candidate as a farther sharper and clearer image.

In the above case, the control device 20 makes the multi-slit element 11 rotate around the axis of the supporting bar member 7 so as to make it withdraw from the optical path of the X rays, and at the same time, changes the angle of the target of the X ray tube so as to change the focal point diameter of the X ray tube 8. Further, in the Talbot-Lau interferometer method, since the objects to be adjusted are somewhat changed, for instance, such that the distance L, which has been adjusted as the distance between the multi-slit element 11 and the first diffraction grating 15 in the Talbot-Lau interferometer method, is adjusted as the distance between the X ray tube 8 and the first diffraction grating 15 after making the multi-slit element 11 withdraw from the optical path of the X rays in the Talbot interferometer method, etc., the positional adjustments of the X ray tube 8, the first diffraction grating 15, the second diffraction grating 16 and the X-ray detector 17 are arbitrarily conducted as needed.

In the case that the Talbot interferometer method is changed to the Talbot-Lau interferometer method, the control device 20 conducts operations being reverse to the above.

As aforementioned, when the radiological image capturing apparatus 1, embodied in the present invention, is employed for the medical use, the apparatus can merely irradiate the X rays having an average energy in a relatively narrow range of 15-60 keV. However, even in such the case, by arranging the second diffraction grating 16 and the X-ray detector 17 so that both of them contact each other, and by specifying the distance L between multi-slit element 11 and the first diffraction grating 15, the distance $Z_1$ between first diffraction grating 15 and the second diffraction grating 16, and the slit interval distance $d_0$ of the multi-slit element 11 as aforementioned, it becomes possible to make the apparatus sufficiently bring out the Talbot effect so as to accurately detect the shapes of the subject H and its inner section in the Moiré stripe image.

Further, when the average energy of the X rays to be irradiated, is smaller than 15 keV, since almost of all part of the irradiated X rays are absorbed into the subject, a dose of X ray exposure for the subject becomes extremely great, and accordingly, such the setting is not suitable for clinical use. However, by setting the average energy of the X rays at a value equal to or greater than 15 keV, it becomes possible not only to avoid such the problem as mentioned in the above, but also to obtain such the X ray image that has no blur caused by the movement of the human body, serving as the subject H, since the operation for irradiating the X rays can be completed within several per second or 2-3 seconds at longest for every time of the single X-ray radiographing operation. Further, by setting the average energy of the X rays to be irradiated at a value equal to or smaller than 60 keV, it becomes possible to acquire such the X-ray radiation image that has sufficient contrasts so as to clearly represent bones, soft tissue sections, etc., which constitute the human body.

As a result, even for the tissue sections, such as the cartilage tissue of the human body, etc., from which the normal-type X-ray radiographing apparatus hardly captures a clear X ray image, it becomes possible to acquire the good X ray image in which the contrast of peripheral sections of the subject is emphasized by employing the Talbot-Lau interferometer method, and therefore, it becomes possible to effectively use the clearly contrasted X ray image acquired in above for the diagnosis purpose or the like.

Further, on that occasion, by making the multi-slit element having a plurality of slits insert into or withdraw from the optical path of the X rays irradiated from the X ray tube, it becomes possible to make the Talbot interferometer method and the Talbot-Lau interferometer method switchable between them. In addition, by appropriately setting the distance between the X ray source or the multi-slit element and the X-ray detector, the other distance between the X ray source or the multi-slit element and the first diffraction grating, the focal point diameter of the X ray tube and the slit interval distance of the multi-slit element, corresponding to each of the abovementioned methods, it becomes possible to obtain a sufficiently clear X ray image within a short X rays irradiation time, while taking advantage of good points possessed by the corresponding one of methods above-mentioned.

For this purpose, for instance, by employing the Talbot-Lau interferometer method to widely radiograph the subject at first, and then, employing the Talbot interferometer method, switched from the Talbot-Lau interferometer method, to radiograph a specific diseased part, etc., so as to acquire its clearer X ray image, it becomes possible to acquire a good X ray image in which the contrast of peripheral sections of the subject is emphasized, even for the operations for radiographing tissue sections from which the normal-type X-ray radiographing apparatus hardly captures a clear X ray image, including not only radiographing the joint disorders, which are represented by the rheumatic disease, but also radiographing various kinds of sections, such as a breast image capturing operation that should be capable of detecting a micro calcification from a breast, most of which is formed by a soft tissue, an operation for radiographing a child body, almost bones of which are cartilages, etc.

Further, since the image processing apparatus 30 of the radiological image capturing system 100 appropriately conducts the various kinds of image processing, it becomes possible to obtain not only the X ray image being clearer than ever, but also the three-dimensional image of the subject H and such the image in which a concerned lesion area is emphasized.

Figure 14:
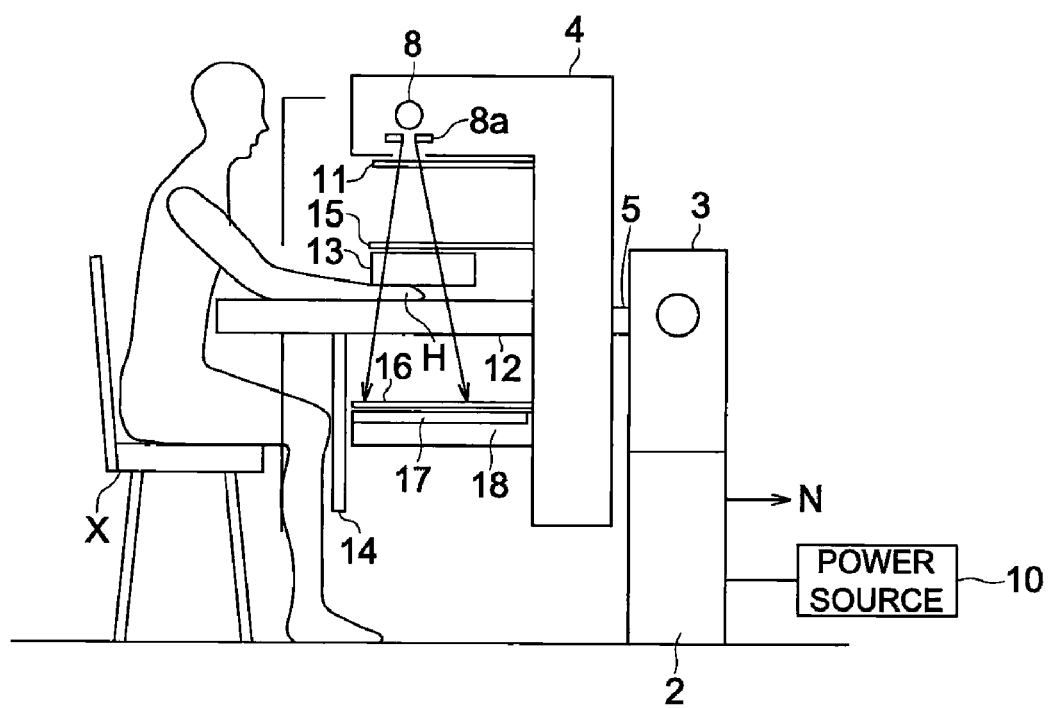
FIG. 14 shows a schematic diagram indicating an exemplary configuration of a radiological image capturing apparatus, which is configured so as to arrange a subject H at a position between a first diffraction grating and a second diffraction grating.

In this connection, instead of the configuration in which the subject placing plate 12, on which the subject H is to be placed, is disposed between the multi-slit element 11 and the first diffraction grating 15 (when the apparatus is used as the Talbot interferometer method, between the X ray tube 8 and the first diffraction grating 15) as structured in the radiological image capturing apparatus 1 embodied in the present invention and shown in FIGS. 2 and 3, for instance, as the radiological image capturing apparatus shown in FIG. 14, it is also applicable that the apparatus is so constituted that the subject placing plate 12, on which the subject H is placed, is disposed between the first diffraction grating 15 and the second diffraction grating 16.

On that occasion, compared to the radiological image capturing apparatus 1 embodied in the present invention, the first diffraction grating 15 closely approaches the multi-slit element 11 and the X ray tube 8. It is necessary that the X rays to be incident into the first diffraction grating should have the coherency property, and for this purpose, an aperture width of each of the slits 111 (namely, a slit width, so to speak) of the multi-slit element 11, which is to be employed when the apparatus is used as the Talbot-Lau interferometer method as shown in FIG. 14, is set at a value in a range of around 1-50 μm, and it is preferable that the slit width is formed at a value in a range of around 7-30 μm. According to the above, the X rays to be incident into the first diffraction grating 15 posses the coherency property and the X rays irradiated from the X ray tube 8 are converted to the multi (plural) radiant sources.

Further, when the apparatus is used as the Talbot interferometer method by rotating the multi-slit element 11, it becomes necessary to set the focal point diameter "a" of the X ray tube 8 at a smaller value. For this reason, the focal point diameter of the X ray tube 8 is set at a value equal to or greater than 0.1 μm, so as to make it possible to irradiate the X rays having an average energy within the abovementioned range and to acquire the output intensity being practically available. Further, when the focal point diameter "a" is set at 1 μm as its minimum value and the average energy of the X rays is set at 60 keV as its maximum value, it is necessary to set the distance L between the X ray tube 8 and the first diffraction grating 15 at a value equal to or greater that 0.5 m. However, since the coherency (coherency distance) is in proportion to the distance L while in inverse proportion to the average energy of the X rays and the focal point diameter, in the case that the coherency is acquired at 60 keV of the X ray average energy, for instance, the distance L between the X ray tube 8 and the first diffraction grating 15 can be set at a value equal to or greater than 0.125 m (12.5 cm) as far as the average energy of the X rays is 15 keV, or, even if the focal point diameter "a" of the X ray tube 8 is widened up to 4 μm, the equivalent degree of the coherency can be obtained. As indicated in the schematic diagram shown in FIG. 14, since the apparatus is so constituted that the first diffraction grating 15 is disposed at the space located between the X ray tube 8 and the subject H, it becomes possible not only to employ such the first diffraction grating 15 that is formed within a small area, resulting in an easiness of the creation working, but also to reduce the influence of slurs, etc., generated in the X ray image and caused by the manufacturing variation of the diffraction grating, etc., and therefore, it becomes possible to acquire the high-resolution X ray image being shaper than ever.

According to the present invention, the following effects can be attained.

(1) It becomes possible to make the apparatus sufficiently exhibit the Talbot effect so as to accurately detect a shape of the subject in the Moiré stripe image. On that occasion, by the converting X rays irradiated from the X ray tube to the multi (plural) radiant sources by employing the multi-slit element, the apparatus is made to be in such a state as if micro focus X ray tubes exist in the apparatus. By employing the multi-slit element having a sufficiently small slit width so as to acquire the Talbot effect, and by employing such an X ray tube that has a large focal diameter so as to acquire high power X rays, it becomes possible to acquire an X ray image without blur caused by the movements of human body, serving as the subject, only by irradiating the X rays in a short time equal to or smaller than several parts of one second. As a result, it becomes possible not only reduce an amount of X ray exposure to be irradiated onto the human body, but also to obtain an image having higher contrast to such an extent that the image can be used for a diagnosis purpose.

(2) By setting a distance between the multi-slit element serving as multi radiant source and the X-ray detector 17, another distance between the multi-slit element and the first diffraction grating, and a slit interval of the multi-slit element, at appropriate values, respectively, it becomes possible to obtain a sufficiently clear X ray image even if the X ray irradiation time is short. Accordingly, it becomes possible to acquire a good X ray image in which the contrast of peripheral sections of the subject is emphasized, by employing the Talbot-Lau interferometer method for the operations for radiographing tissue sections from which the normal-type X-ray radiographing apparatus hardly captures a clear X ray image, including not only radiographing the joint disorders, which are represented by the rheumatic disease, but also radiographing various kinds of sections, such as a breast image capturing operation that should be capable of detecting a micro calcification from a breast, most of which is formed by a soft tissue, an operation for radiographing a child body, almost bones of which are cartilages, etc.

The invention claimed is:

1. A radiological image capturing apparatus for capturing a radiological image of a joint portion, comprising:
   an X ray tube to emit first X rays;
   an element located in a vicinity of the X ray tube, so as to convert the first X rays emitted by the X ray tube to second X rays that are to be emitted from multi radiant sources;
   a subject placing plate to place the joint portion thereon;
   a first diffraction grating and a second diffraction grating, arranged so as to yield a Talbot effect; and
   an X ray detector to detect third X rays through the second diffraction grating;
   wherein the X ray tube, the element, the subject placing plate, the first diffraction grating, the second diffraction grating and the X ray detector are arranged in a vertical direction orthogonal to a floor on which the radiological image capturing apparatus is installed;
   wherein positions of the X ray tube, the element, the subject placing plate, the first diffraction grating, the second diffraction grating and the X-ray detector, relative to the joint portion, are kept constant in such a state that they overlap with each other along the vertical direction concerned, during a time when an operation for radiographing the joint portion, placed onto the subject placing plate, is implemented; and
   wherein the subject placing plate is disposed at a space located between the element and the first diffraction grating, in such a manner that a radiological technician on the floor can visually recognize a direction of the joint portion with respect to the subject placing plate.

2. The radiological image capturing apparatus of claim 1, wherein the subject placing plate is protruded beyond an area of the first grating so that the joint portion is kept stable, while another portion, located next to the joint portion, is kept resting on the subject placing plate.

* * * * *